US010106521B2

(12) United States Patent
Shin et al.

(10) Patent No.: US 10,106,521 B2
(45) Date of Patent: Oct. 23, 2018

(54) ECKOL DERIVATIVES, METHODS OF SYNTHESIS AND USES THEREOF

(71) Applicant: Phloronol, Inc., San Francisco, CA (US)

(72) Inventors: Hyeon-Cheol Shin, Bonney Lake, WA (US); Hyejeong Hwang, Bonney Lake, WA (US); Kwang Yong Park, Seoul (KR); Seong Ho Kim, Daejeon (KR); Haengwoo Lee, Bellevue, WA (US)

(73) Assignee: Phloronol, Inc., Portland, OR (US)

( * ) Notice: Subject to any disclaimer, the term of this patent is extended or adjusted under 35 U.S.C. 154(b) by 0 days.

(21) Appl. No.: 15/808,790

(22) Filed: Nov. 9, 2017

(65) Prior Publication Data

US 2018/0127392 A1 May 10, 2018

Related U.S. Application Data

(60) Provisional application No. 62/419,914, filed on Nov. 9, 2016.

(51) Int. Cl.
*C07D 319/24* (2006.01)
*C07D 493/04* (2006.01)

(52) U.S. Cl.
CPC ......... *C07D 319/24* (2013.01); *C07D 493/04* (2013.01)

(58) Field of Classification Search
CPC ........................... C07D 319/24; C07D 493/04
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,710,795 A | 1/1973 | Higuchi et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,891,474 A | 4/1999 | Busetti et al. |
| 5,900,252 A | 5/1999 | Calanchi et al. |
| 5,922,356 A | 7/1999 | Koseki et al. |
| 5,948,433 A | 9/1999 | Burton et al. |
| 5,972,366 A | 10/1999 | Haynes et al. |
| 5,972,891 A | 10/1999 | Kamei et al. |
| 5,980,945 A | 11/1999 | Ruiz |
| 5,983,134 A | 11/1999 | Ostrow |
| 5,985,307 A | 11/1999 | Hanson et al. |
| 5,985,317 A | 11/1999 | Venkateshwaran et al. |
| 5,993,855 A | 11/1999 | Yoshimoto et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |

(Continued)

FOREIGN PATENT DOCUMENTS

WO 2005/025506 A2 3/2005

OTHER PUBLICATIONS

Y. Fukuyama et al., 37 Chemical & Pharmaceutical Bulletin, 349-353 (1989).*
International Search Report in corresponding PCT/US2017/060943, dated Jan. 25, 2018.
"Pubchem CID 44575550" Create Date: Jan. 26, 2010 Date Accessed: Jan. 8, 2018; p. 4, compound listed, p. 12.
Ahn et al. "Neuroprotective effect of edible brown alga *Eisenia bicyclis* on amyloid beta peptide-induced toxicity in PC12 cells" Archives of Pharmaceutical Research. Dec. 4, 2012, vol. 35, p. 1989-1998; abstract.
"Pubchem AID 399514" Create Date: May 15, 2010 Date Accessed: Jan. 8, 2018; p. 3, abstract.

(Continued)

*Primary Examiner* — Alexander R Pagano
(74) *Attorney, Agent, or Firm* — Young Basile Hanlon & MacFarlane, P.C.

(57) ABSTRACT

Provided herein are eckol derivatives, methods of synthesis thereof and pharmaceutical compositions thereof. In other embodiments, provided herein are methods of treatment, prevention, or amelioration of a variety of medical disorders such as, for example, Alzheimer's disease, microbial infections, obesity, diabetes, cancer or inflammation using the compounds and pharmaceutical compositions disclosed herein.

39 Claims, No Drawings

(56) References Cited

U.S. PATENT DOCUMENTS

| | | | |
|---|---|---|---|
| 6,131,570 | A | 10/2000 | Schuster et al. |
| 6,139,865 | A | 10/2000 | Friend et al. |
| 6,167,301 | A | 12/2000 | Flower et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,264,970 | B1 | 7/2001 | Hata et al. |
| 6,267,981 | B1 | 7/2001 | Okamoto et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 2005/0101660 | A1* | 5/2005 | Lee ................ A61K 31/335 514/452 |

OTHER PUBLICATIONS

"Pubchem CID 16132364" Create Date: Jul. 3, 2007 Date Accessed: Jan. 8, 2018; p. 3, compound listed.

Martinez et al. "Preparation and Chromatographic Analysis of Phlorotannins" Journal of Chromatographic Science. Apr. 16, 2013, vol. 51, p. 825-838; p. 5, figure 8, p. 9, figure 12.

Guillory, K., Chapter 5, pp. 202-205 in Polymorphism in Pharmaceutical Solids, (Brittain, H. ed.), Marcel Dekker, Inc., New York, NY, 1999).

Brittain, H., Chapter 6, pp. 205208 in Polymorphism in Pharmaceutical Solids, (Brittain, H. ed.).

Carstensen, Jens T., Drug Stability: Principles & Practice, 2d. Ed., Marcel Dekker, NY, NY, (1995), pp. 379-380.

Sefton, M. Implantable Pumps. CRC Crit. Ref. Biomed. Eng. 14:201 (1987).

Goodson, Medical Applications of Controlled Release, vol. 2, pp. 115-138 (1984).

Langer, R. New Methods of Drug Delivery. Science 249:1527-1533 (1990).

Buchwald et al., Implantable Infusion Pump Management of Insulin Resistant Diabetes Mellitus. Surgery 88:507 (1980).

Saudek, et al. N. Engl. J. Med. 321: 574 (1989).

\* cited by examiner

ECKOL DERIVATIVES, METHODS OF SYNTHESIS AND USES THEREOF

CROSS-REFERENCE TO RELATED APPLICATION

This application claims priority under 35 U.S.C. § 119 (e) from U.S. Provisional Application Ser. No. 62/419,914, filed Nov. 9, 2016, which is hereby incorporated by reference in its entirety.

FIELD

Provided herein are eckol derivatives, methods of synthesis thereof and pharmaceutical compositions thereof. In other embodiments, provided herein are methods of treatment, prevention, or amelioration of a variety of medical disorders such as, for example, Alzheimer's disease, microbial infections, obesity, diabetes, cancer or inflammation using the compounds and pharmaceutical compositions disclosed herein.

BACKGROUND

Eckols are a special class of polyphenols derived from brown algae, which are known as phlorotannins and are characterized by a dibenzo-1,4-dioxin unit in the molecular skeleton which is found only in some specific algae such as *Eisenia* and *Ecklonia* species. Importantly, eckols have the unusual ability to penetrate the blood brain barrier and have a diverse array of biological activities.

Exemplary eckols include 2-O-(2,4,6-trihydroxyphenyl) 6,6' bieckol, 6,6' bieckol, 8,8, bieckol, phlorofucofuroeckol A, fucofuroeckol A, dioxinodehydroeckol, dieckol, eckol, 2-phloroeckol and 7-phloroeckol, the structures of which are depicted below.

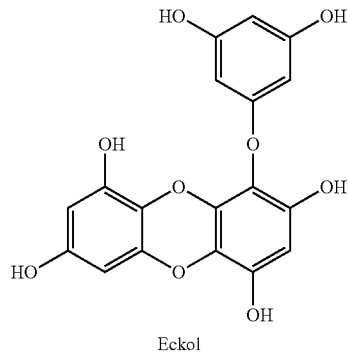

Eckol

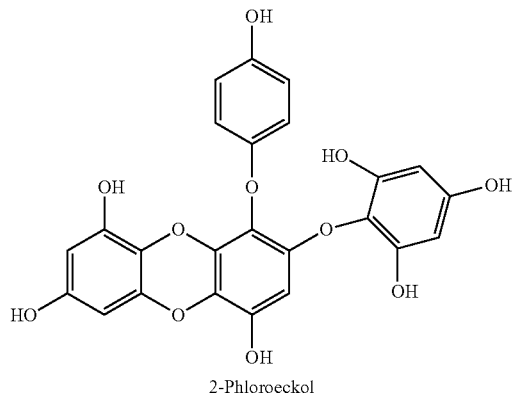

2-Phloroeckol

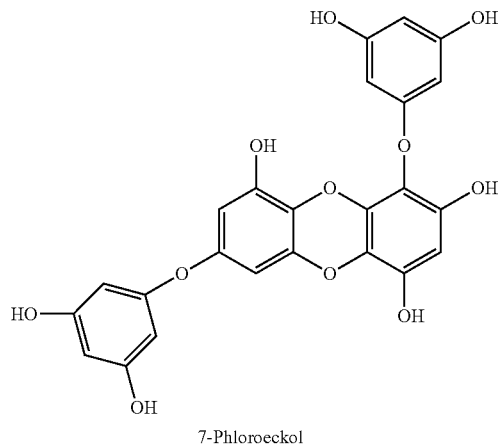

7-Phloroeckol

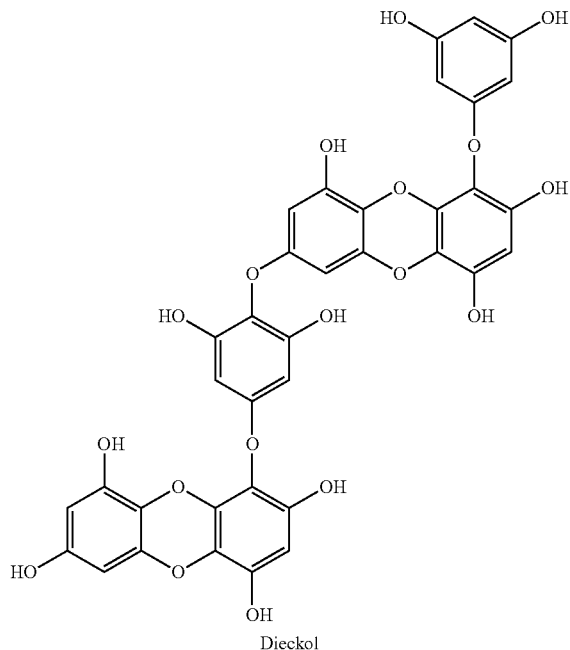

Dieckol

-continued
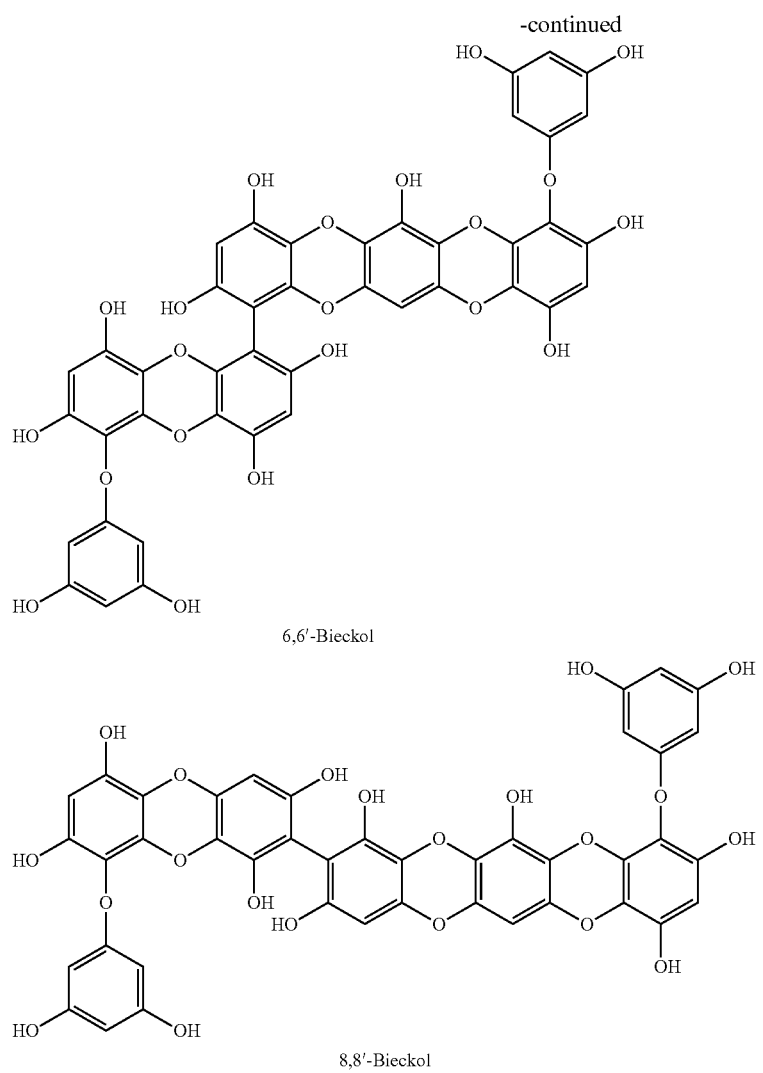
6,6'-Bieckol
8,8'-Bieckol
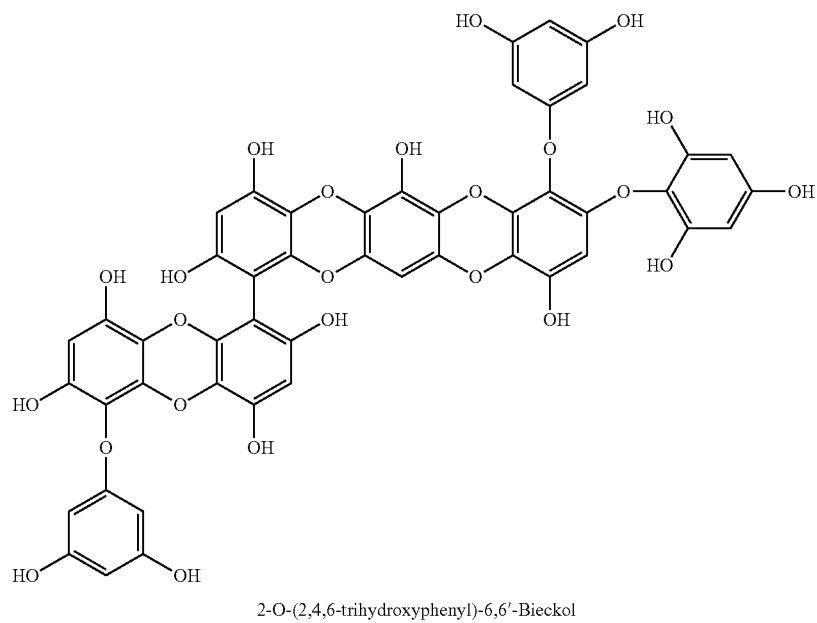
2-O-(2,4,6-trihydroxyphenyl)-6,6'-Bieckol -continued

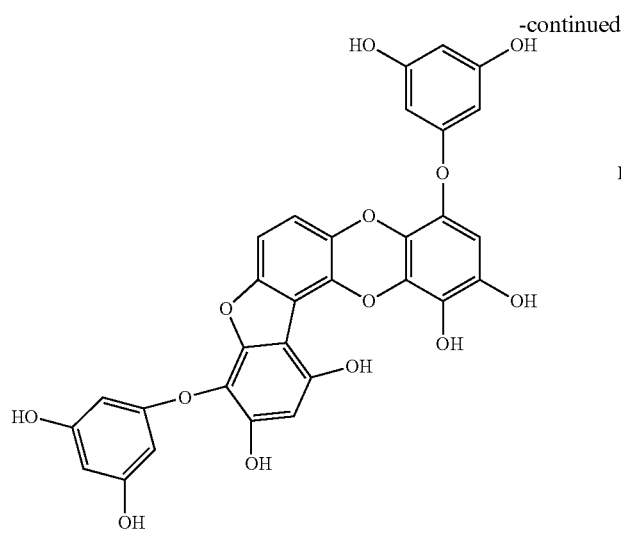

Phlorofucofuroeckol A

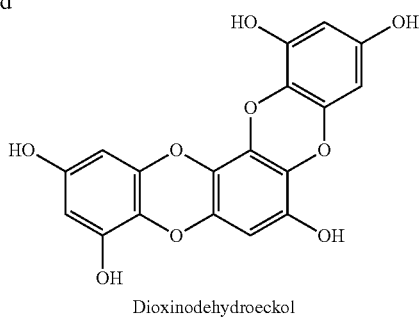

Dioxinodehydroeckol

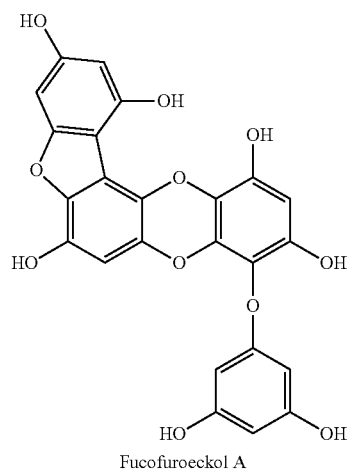

Fucofuroeckol A

Noteworthy of the above structures is that the eckols, in general, all possess the core structure of eckol, which is regioselectively modified with additional phenolic groups to provide the compounds above.

Given the impressive biological activity of the natural eckols, it is necessary to prepare synthetically modified eckols which may possess superior biological activity against various medical disorders.

SUMMARY

Provided herein are eckol derivatives which address these and other needs. In one aspect, a compound of Formula (I) is provided:

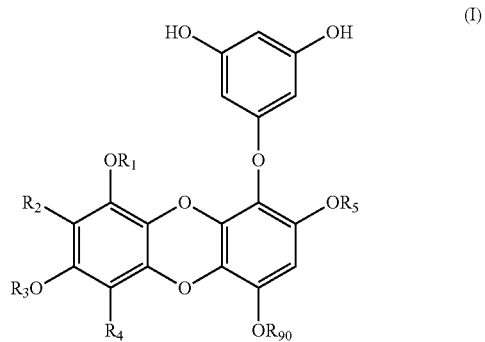

or salts, solvates, hydrates thereof wherein:

$R_1$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$, $R_{11}OC(O)$, $R_{12}R_{13}NC(O)$, $R_{14}(R_{15}O)(O)P$, $(R_{16}O)(R_{17}O)(O)P$ or $R_{18}R_{19}R_{20}Si$;

$R_2$ is hydrogen or

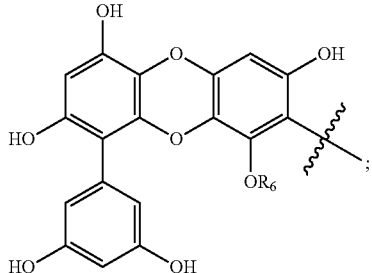

$R_3$ is hydrogen,

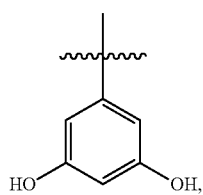

or a bond which forms a five-membered ether ring with the carbon atom adjacent to $R_8$ when $R_4$ is

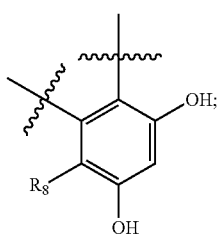

$R_4$ is hydrogen or

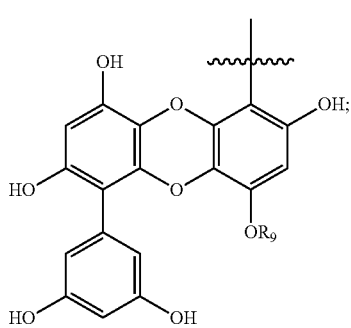

$R_5$ is hydrogen, or

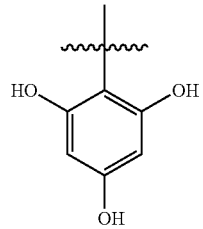

or a bond which forms a six membered dioxane ring with the ortho carbon of the adjacent 3,5 dihydroxy phenyl substituent;

$R_6$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{30}C(O)$, $R_{31}OC(O)$, $R_{32}NR_{33}C(O)$, $R_{34}(R_{35}O)(O)P$, $(R_{36}O)(R_{37}O)(O)P$ or $R_{38}R_{39}R_{40}Si$;

$R_7$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{50}C(O)$, $R_{51}OC(O)$, $R_{52}NR_{53}C(O)$, $R_{54}(R_{55}O)(O)P$, $(R_{56}O)(R_{57}O)(O)P$ or $R_{58}R_{59}R_{60}Si$;

$R_8$ is hydrogen or

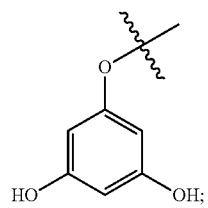 [SMILES: *Oc1cc(O)cc(O)c1]

and $R_9$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{70}C(O)$, $R_{71}OC(O)$, $R_{72}NR_{73}C(O)$, $R_{74}(R_{75}O)(O)P$, $(R_{76}O)(R_{77}O)(O)P$ or $R_{78}R_{79}R_{80}Si$;

$R_{90}$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{100}C(O)$, $R_{101}OC(O)$, $R_{102}NR_{103}C(O)$, $R_{104}(R_{105}O)(O)P$, $(R_{106}O)(R_{107}O)(O)P$ or $R_{108}R_{109}R_{110}Si$;

provided that at least three of $R_1$-$R_5$ are hydrogen, except when $R_4$ is

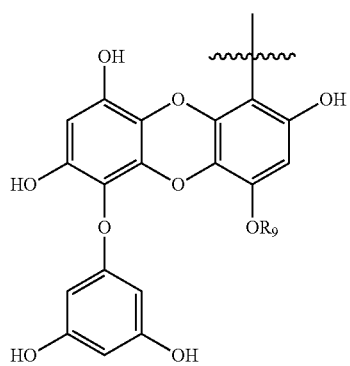

and $R_5$ is

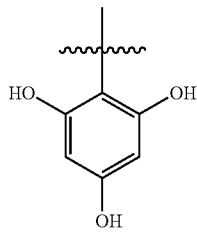

or when $R_3$ is a bond which forms a five membered ether ring with the carbon atom adjacent to $R_8$ when $R_4$ is

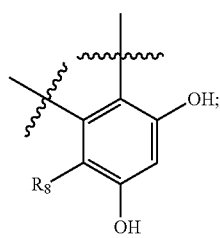

provided that $R_1$ is not hydrogen when $R_6$, $R_7$ or $R_9$ are hydrogen, when $R_2$, $R_3$ and $R_4$ are hydrogen and when $R_2$ is hydrogen and $R_3$ is a bond which forms a five-membered ether ring with the carbon atom adjacent to $R_8$ when $R_4$ is

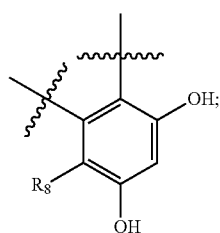

and provided that $R_{90}$ is hydrogen except when $R_3$ is a bond which forms a five-membered ether ring with the carbon atom adjacent to $R_8$ when $R_4$ is

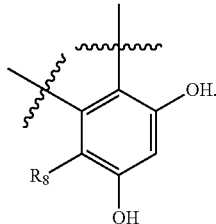

Also provided are derivatives, including salts, esters, enol ethers, enol esters, solvates, hydrates, metabolites and prodrugs of the compounds described herein. Further provided are pharmaceutical compositions which include the compounds provided herein and a pharmaceutically acceptable vehicle.

Methods of treating, preventing, or ameliorating symptoms of medical disorders such as, for example, Alzheimer's disease, Parkinson's disease, stroke, microbial infections (i.e., fungal viral, bacterial), circulatory issues (e.g., plasmin inhibition, hypertension, thrombosis, etc.), metabolic disorders (e.g., hypolipidemia, obesity, diabetes, etc.), coronary artery disease, allergic response (e.g., histamine release, IgE receptor response, airway hypersensitiveness, etc.), enzyme activity (e.g., excessive matrix metalloprotease, hyaluronidase, elastase, cholinesterase, tyrosinase activity), arthritis, oral disease, hair and scalp disease, virility issues, skin disease, inflammation (e.g., reduction in NfkB, COX iNOS, treatment of sepsis etc.), fibromyalgia, cancer and neuralgia are provided herein. In addition, methods of neuroprotection (i.e., reduction of beta amyloid production) and cellular protection (e.g., protection from oxidation and radiation, protection of liver cells) are also provided herein. Furthermore, the eckol derivatives described herein can inhibit enzymes associated with Alzheimer's disease (e.g., acetylcholinesterase, butrylcholinesterase, beta secretase 1, etc.). In practicing the methods, therapeutically effective amounts of the compounds or pharmaceutical compositions thereof are administered to a subject.

DETAILED DESCRIPTION

Definitions

Unless defined otherwise, all technical and scientific terms used herein have the same meaning as is commonly understood by one of ordinary skill in the art to which this invention belongs. If there are a plurality of definitions for a term herein, those in this section prevail unless stated otherwise.

"Alkyl" by itself or as part of another substituent, refers to a saturated or unsaturated, branched, straight chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propanlyl, propan2yl, cyclopropanlyl, proplenlyl, proplen2yl, prop2enlyl (allyl), cycloproplenlyl; cycloprop2enlyl, proplynlyl, prop2ynlyl, etc.; butyls such as butanlyl, butan2yl, 2methylpropanlyl, 2methylpropan2yl, cyclobutanlyl, butlenlyl, butlen2yl, 2methylproplenlyl, but2enlyl, but2en2yl, butal,3dienlyl, butal,3dien2yl, cyclobutlenlyl, cyclobutlen3yl, cyclobutal,3dienlyl, butlynlyl, butlyn3yl, but3ynlyl, etc.; and the like. The term "alkyl" is specifically intended to include groups having any degree or level of saturation, i.e., groups having exclusively single carbon carbon bonds, groups having one or more double carbon carbon bonds, groups having one or more triple carbon carbon bonds and groups having mixtures of single, double and triple carbon carbon bonds. Where a specific level of saturation is intended, the expressions "alkanyl," "alkenyl," and "alkynyl" are used. In some embodiments, an alkyl group comprises from 1 to 20 carbon atoms ($C_1C_{20}$ alkyl). In other embodiments, an alkyl group comprises from 1 to 10 carbon atoms ($C_1C_{10}$ alkyl). In still other embodiments, an alkyl group comprises from 1 to 6 carbon atoms ($C_1C_6$ alkyl).

"Alkanyl" by itself or as part of another substituent, refers to a saturated branched, straight chain or cyclic alkyl radical derived by the removal of one hydrogen atom from a single carbon atom of a parent alkane. Typical alkanyl groups include, but are not limited to, methanyl; ethanyl; propanyls such as propanlyl, propan2yl (isopropyl), cyclopropanlyl, etc.; butanyls such as butanlyl, butan2yl (sec-butyl), 2methylpropanlyl (isobutyl), 2methylpropan2yl (t-butyl), cyclobutanlyl, etc.; and the like.

"Alkenyl" by itself or as part of another substituent, refers to an unsaturated branched, straight chain or cyclic alkyl radical having at least one carbon carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as proplenlyl, proplen2yl, prop2enlyl (allyl), prop2en2yl, cycloproplenlyl; cycloprop2enlyl; butenyls such as butlenlyl, butlen2yl, 2methylproplenlyl, but2enlyl, but2enlyl, but2en2yl, butal, 3dienlyl, butal,3dien2yl, cyclobutlenlyl, cyclobutlen3yl, cyclobutal,3dienlyl, etc.; and the like.

"Alkynyl" by itself or as part of another substituent refers to an unsaturated branched, straight chain or cyclic alkyl radical having at least one carbon carbon triple bond derived by the removal of one hydrogen atom from a single carbon atom of a parent alkyne. Typical alkynyl groups include, but are not limited to, ethynyl; propynyls such as proplynlyl, prop2ynlyl, etc.; butynyls such as butlynlyl, butlyn3yl, but3ynlyl, etc.; and the like.

"Acyl" by itself or as part of another substituent refers to a radical $C(O)R^{400}$ where $R^{400}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl" by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, asindacene, sindacene, indane, indene, naphthalene, octacene, octaphene, octalene, ovalene, penta2,4diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6C_{20}$ aryl). In other embodiments, an aryl group comprises from 6 to 15 carbon atoms ($C_6C_{15}$ aryl). In still other embodiments, an aryl group comprises from 6 to 15 carbon atoms ($C_6C_{10}$ aryl).

"Arylalkyl" by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2phenylethanlyl, 2phenylethenlyl, naphthylmethyl, 2naphthylethanlyl, 2naphthylethenlyl, naphthobenzyl, 2naphthophenylethanlyl and the like. Where specific alkyl moieties are intended, the nomenclature arylalkanyl, arylalkenyl and/or arylalkynyl is used. In some embodiments, an arylalkyl group is ($C_6C_{30}$) arylalkyl, e.g., the alkanyl, alkenyl or alkynyl moiety of the arylalkyl group is ($C_1C_{10}$) alkyl and the aryl moiety is ($C_6C_{20}$) aryl. In other embodiments, an arylalkyl group is ($C_6C_{20}$) arylalkyl, e.g., the alkanyl, alkenyl or alkynyl moiety of the arylalkyl group is ($C_1C_8$) alkyl and the aryl moiety is ($C_6C_{12}$) aryl. In still other embodiments, an arylalkyl group is ($C_6C_{15}$) arylalkyl, e.g., the alkanyl, alkenyl or alkynyl moiety of the arylalkyl group is ($C_1C_5$) alkyl and the aryl moiety is ($C_6C_{10}$) aryl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds described herein include, but are not limited to, $^2H$, $^3H$, $^{13}C$, $^{14}C$, $^{15}N$, $^{18}O$, $^{17}O$, $^{35}S$, etc. In general, it should be understood, that all isotopes of any of the elements comprising the compounds described herein may be found in these compounds. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Heteroalkyl," "Heteroalkanyl," "Heteroalkenyl" and "Heteroalkynyl" by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, O, S, N, Si, NH, S(O), S(O)$_2$, S(O)NH, S(O)$_2$NH and the like and combinations thereof. The heteroatoms or heteroatomic groups may be placed at any interior position of the alkyl, alkenyl or alkynyl groups. Typical heteroatomic groups which can be included in these groups include, but are not limited to, O, S, OO, SS, OS, NR$^{501}$R$^{502}$, =NN=, N=N, N=NNR$^{503}$R$^{54}$, PR$^{505}$, P(O)$_2$, POR$^{506}$, OP(O)$_2$, SO$_2$, SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, βcarboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (520 membered heteroaryl). In other embodiments, the heteroaryl group comprises from 5 to 10 ring atoms (510 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 621 membered heteroarylalkyl, e.g., the alkanyl, alkenyl or alkynyl moiety of the heteroarylalkyl is (C$_1$C$_6$) alkyl and the heteroaryl moiety is a 515membered heteroaryl. In other embodiments, the heteroarylalkyl is a 613 membered heteroarylalkyl, e.g., the alkanyl, alkenyl or alkynyl moiety is (C$_1$C$_3$) alkyl and the heteroaryl moiety is a 510 membered heteroaryl.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, asindacene, sindacene, indane, indene, naphthalene, octacene, octaphene, octalene, ovalene, penta2,4diene, pentacene, pentalene, pentaphene, perylene, phenalene, phenanthrene, picene, pleiadene, pyrene, pyranthrene, rubicene, triphenylene, trinaphthalene and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as 'prophylaxis.' In some embodiments, the compounds provided herein provide superior prophylaxis because of lower long term side effects over long time periods.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4chlorobenzenesulfonic acid, 2naphthalenesulfonic acid, 4-toluenesulfonic acid, camphorsulfonic acid, 4-methylbicyclo[2.2.2] oct2enelcarboxylic acid, glucoheptonic acid, 3phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In some embodiments, the salt is pharmaceutically acceptable.

"Solvates" refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205208 in *Polymorphism in Pharmaceutical Solids*, (Brittain, H. ed.), Marcel Dekker, Inc., New York, N.Y., 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted" when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to $R^a$, halo, O, =O, $OR^b$, $SR^b$, S, =S, $NR^cR^c$, $=NR^b$, $=NOR^b$, trihalomethyl, $CF_3$, CN, OCN, SCN, NO, $NO_2$, $=N_2$, $N_3$, $S(O)_2R^b$, $S(O)_2NR^b$, $S(O)_2O$, $S(O)_2OR^b$, $OS(O)_2R^b$, $OS(O)_2O$, $OS(O)_2OR^b$, $P(O)(O)_2$, $P(O)(OR^b)(O)$, $P(O)(OR^b)(OR^b)$, $C(O)R^b$, $C(S)R^b$, $C(NR^b)R^b$, C(O)O, $C(O)OR^b$, $C(S)OR^b$, $C(O)NR^cR^c$, $C(NR^b)NR^cR^c$, $OC(O)R^b$, $OC(S)R^b$, OC(O)O, $OC(O)OR^b$, $OC(S)OR^b$, $NR^bC(O)R^b$, $NR^bC(S)R^b$, $NR^bC(O)O$, $NR^bC(O)OR^b$, $NR^bC(S)OR^b$, $NR^bC(O)NR^cR^c$, $NR^bC(NR^b)R^b$ and $NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$'s are taken together with the nitrogen atom to which they are bonded form a 4, 5, 6 or 7membered cycloheteroalkyl which may optionally include from 1 to 4 of the same or different additional heteroatoms selected from the group consisting of O, N and S. As specific examples, $NR^cR^c$ is meant to include $NH_2$, NH-alkyl, N-pyrrolidinyl and N-morpholinyl.

Similarly, substituent groups useful for substituting unsaturated carbon atoms in the specified group or radical include, but are not limited to, $R^a$, halo, O, $OR^b$, $SR^b$, S, $NR^cR^c$, trihalomethyl, $CF_3$, CN, OCN, SCN, NO, $NO_2$, $N_3$, $S(O)_2R^b$, $S(O)_2O$, $S(O)_2OR^b$, $OS(O)_2R^b$, $OS(O)_2O$, $OS(O)_2OR^b$, $P(O)(O)_2$, $P(O)(OR^b)(O)$, $P(O)(OR^b)(OR^b)$, $C(O)R^b$, $C(S)R^b$, $C(NR^b)R^b$, C(O)O, $C(O)OR^b$, $C(S)OR^b$, $C(O)NR^cR^c$, $C(NR^b)NR^cR^c$, $OC(O)R^b$, $OC(S)R^b$, OC(O)O, $OC(O)OR^b$, $OC(S)OR^b$, $NR^bC(O)R^b$, $NR^bC(S)R^b$, $NR^bC(O)O$, $NR^bC(O)OR^b$, $NR^bC(S)OR^b$, $NR^bC(O)NR^cR^c$, $NR^bC(NR^b)R^b$ and $NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, $R^a$, O, $OR^b$, $SR^b$, S, $NR^cR^c$, trihalomethyl, $CF_3$, CN, NO, $NO_2$, $S(O)_2R^b$, $S(O)_2O$, $S(O)_2OR^b$, $OS(O)_2R^b$, $OS(O)_2O$, $OS(O)_2OR^b$, $P(O)(O)_2$, $P(O)(OR^b)(O)$, $P(O)(OR^b)(OR^b)$, $C(O)R^b$, $C(S)R^b$, $C(NR^b)R^b$, $C(O)OR^b$, $C(S)OR^b$, $C(O)NR^cR^c$, $C(NR^b)NR^cR^c$, $OC(O)R^b$, $OC(S)R^b$, $OC(O)OR^b$, $OC(S)OR^b$, $NR^bC(O)R^b$, $NR^bC(S)R^b$, $NR^bC(O)OR^b$, $NR^bC(S)OR^b$, $NR^bC(O)NR^cR^c$, $NR^bC(NR^b)R^b$ and $NR^bC(NR^b)NR^cR^c$, where $R^a$, $R^b$ and $R^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above. In some embodiments, substituents are limited to the groups above.

"Subject," "individual" or "patient" is used interchangeably herein and refers to a vertebrate, preferably a mammal. Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof,). Treatment may also be considered to include preemptive or prophylactic administration to ameliorate, arrest or prevent the development of the disease or at least one of the clinical symptoms. Treatment can also refer to the lessening of the severity and/or the duration of one or more symptoms of a disease or disorder. In a further feature, the treatment rendered has lower potential for long term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, adsorption, distribution, metabolism and excretion etc., of the patient to be treated.

"Vehicle" refers to a diluent, excipient or carrier with which a compound is administered to a subject. In some embodiments, the vehicle is pharmaceutically acceptable.

Compounds

Disclosed herein is a compound of Formula (I):

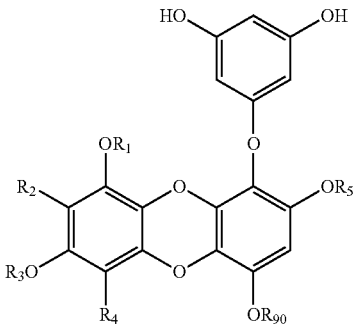

or salts, solvates, hydrates thereof wherein:

$R_1$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$, $R_{11}OC(O)$, $R_{12}R_{13}NC(O)$, $R_{14}(R_{15}O)(O)P$, $(R_{16}O)(R_{17}O)(O)P$ or $R_{18}R_{19}R_{20}Si$;

$R_2$ is hydrogen or

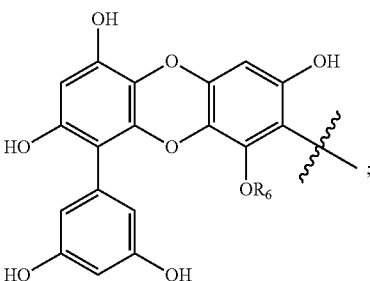

$R_3$ is hydrogen,

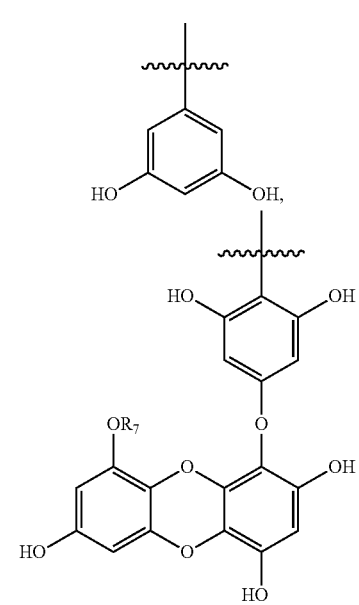

or a bond which forms a five membered ether ring with the carbon atom adjacent to $R_8$ when $R_4$ is

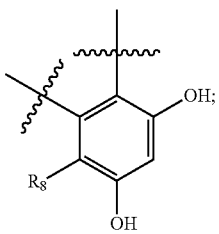

$R_4$ is hydrogen or

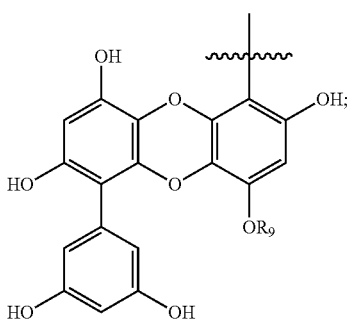

$R_5$ is hydrogen,

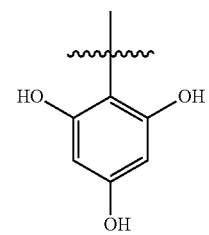

or a bond which forms a six membered dioxane ring with the ortho carbon of the adjacent 3,5 dihydroxy phenyl substituent;

$R_6$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{30}C(O)$, $R_{31}OC(O)$, $R_{32}NR_{33}C(O)$, $R_{34}(R_{35}O)(O)P$, $(R_{36}O)(R_{37}O)(O)P$ or $R_{38}R_{39}R_{40}Si$;

$R_7$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{50}C(O)$, $R_{51}OC(O)$, $R_{52}NR_{53}C(O)$, $R_{54}(R_{55}O)(O)P$, $(R_{56}O)(R_{57}O)(O)P$ or $R_{58}R_{59}R_{60}Si$;

$R_8$ is hydrogen or

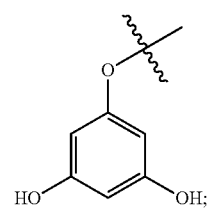 [SMILES: *Oc1cc(O)cc(O)c1]

and

R$_9$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, R$_{70}$C(O), R$_{71}$OC(O), R$_{72}$NR$_{73}$C(O), R$_{74}$(R$_{75}$O)(O)P, (R$_{76}$O)(R$_{77}$O)(O)P or R$_{78}$R$_{79}$R$_{80}$Si;

R$_{90}$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, R$_{100}$C(O), R$_{101}$C(O), R$_{102}$NR$_{103}$C(O), R$_{104}$(R$_{105}$O)(O)P, (R$_{106}$O)(R$_{107}$O)(O)P or R$_{108}$R$_{109}$R$_{110}$Si;

provided that at least three of R$_1$-R$_5$ are hydrogen, except when R$_4$ is

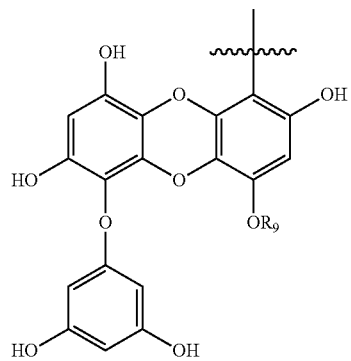

and R$_5$ is

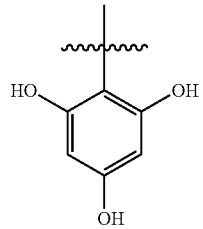

or when R$_3$ is a bond which forms a five membered ether ring with the carbon atom adjacent to R$_8$ when R$_4$ is

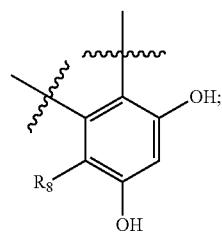

provided that R$_1$ is not hydrogen when R$_6$, R$_7$ or R$_9$ are hydrogen, when R$_2$, R$_3$ and R$_4$ are hydrogen and when R$_2$ is hydrogen and R$_3$ is a bond which forms a five-membered ether ring with the carbon atom adjacent to R$_8$ when R$_4$ is

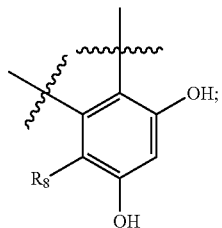

and provided that R$_{90}$ is hydrogen except when R$_3$ is a bond which forms a five-membered ether ring with the carbon atom adjacent to R$_8$ when R$_4$ is

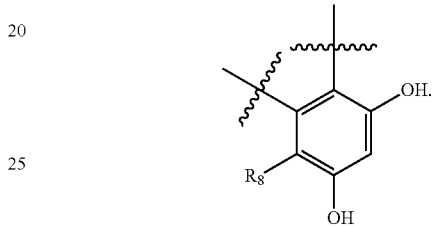

In some embodiments, at most three of R$_1$-R$_5$ are hydrogen, except when R$_4$ is

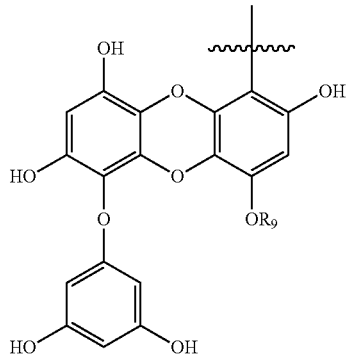

and R$_5$ is

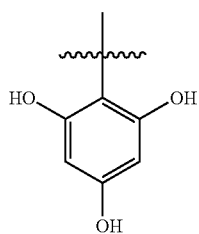

or when R$_3$ is a bond which forms a five membered ring with the carbon atom adjacent to R$_8$ when R$_4$ is

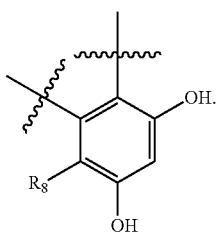

In some embodiments, the compounds of Formula (I) do not include Eckol, 2-Phloroeckol, 7-Pholoroeckol, Dieckol, 6,6'-Bieckol, 8,8' Bieckol, 2-O-(2,4,6-trihydroxyphenyl)-6,6' Bieckol, Fucofuroeckol A, Phlorofucofuroeckol A and dioxinohydroeckol. In other embodiments, the compounds of Formula (I) do not include Eckol, 2-Phloroeckol, 7-Pholoreckol, Dieckol, 6,6'-Bieckol, 8,8' Fucofuroeckol A and Phlorofucofuroeckol A. In still other embodiments, the compounds of Formula (I) do not include Eckol, 2-Phloroeckol, 7-Pholoreckol, Dieckol, 6,6'-Bieckol, 8,8' Bieckol, Phlorofucofuroeckol A and dioxinohydroeckol. In still other embodiments, the compounds of Formula (I) do not include Eckol, 2-Phloroeckol, 7-Pholoreckol, Dieckol, 6,6'-Bieckol, 8,8' Bieckol and Phlorfucofuroeckol A. In still other embodiments, the compounds of Formula (I) do not include Eckol. In still other embodiments, the compounds of Formula (I) do not include 2-Phloroeckol. In still other embodiments, the compounds of Formula (I) do not include Dieckol. In still other embodiments, the compounds of Formula (I) do not include 6,6'-Bieckol. In still other embodiments, the compounds of Formula (I) do not include 8,8' Bieckol. In still other embodiments, the compounds of Formula (I) do not include 2-O-(2,4,6-trihydroxyphenyl)-6,6' Bieckol. In still other embodiments, the compounds of Formula (I) do not include Fucofuroeckol A. In still other embodiments, the compounds of Formula (I) do not include Phlorofucofuroeckol A. In some embodiments, the compounds of Formula (I) do not include dioxinohydroeckol.

In some embodiments, $R_1$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$, $R_{11}OC(O)$ or $R_{12}NR_{13}C(O)$. In other embodiments, $R_1$ is hydrogen, alkyl, substituted alkyl, aryl, substituted aryl, arylalkyl, substituted arylalkyl, heteroalkyl or $R_{10}C(O)$. In still other embodiments, $R_1$ is hydrogen, alkyl, arylalkyl, heteroalkyl or $R_{10}C(O)$. In still other embodiments, $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_1$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$, $R_{11}OC(O)$ or $R_{12}NR_{13}C(O)$. In other embodiments, $R_1$ is alkyl, substituted alkyl, aryl, substituted aryl, arylalkyl, substituted arylalkyl, heteroalkyl or $R_{10}C(O)$. In still other embodiments, $R_1$ is alkyl, arylalkyl, heteroalkyl or $R_{10}C(O)$. In still other embodiments, $R_1$ is —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_6$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{30}C(O)$, $R_{31}OC(O)$ or $R_{32}NR_{33}C(O)$. In other embodiments, $R_6$ is hydrogen, alkyl, substituted alkyl, aryl, substituted aryl, arylalkyl, substituted arylalkyl, heteroalkyl or $R_{30}C(O)$. In still other embodiments, $R_6$ is hydrogen, alkyl, arylalkyl, heteroalkyl or $R_{30}C(O)$. In still other embodiments, $R_6$ is hydrogen, —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_6$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{30}C(O)$, $R_{31}OC(O)$ or $R_{32}NR_{33}C(O)$. In other embodiments, $R_6$ is alkyl, substituted alkyl, aryl, substituted aryl, arylalkyl, substituted arylalkyl, heteroalkyl or $R_{30}C(O)$. In still other embodiments, $R_6$ is alkyl, arylalkyl, heteroalkyl or $R_{30}C(O)$. In still other embodiments, $R_1$ is alkyl, arylalkyl, heteroalkyl or $R_{10}C(O)$. In still other embodiments, $R_6$ is —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_7$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{50}C(O)$, $R_{10}OC(O)$ or $R_{52}NR_{53}C(O)$. In other embodiments, $R_7$ is hydrogen, alkyl, substituted alkyl, aryl, substituted aryl, arylalkyl, substituted arylalkyl, heteroalkyl or $R_{50}C(O)$. In still other embodiments, $R_7$ is hydrogen, alkyl, arylalkyl, heteroalkyl or $R_{50}C(O)$. In still other embodiments, $R_7$ is hydrogen, —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_7$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{50}C(O)$, $R_{51}OC(O)$ or $R_{52}NR_{53}C(O)$. In other embodiments, $R_7$ is alkyl, substituted alkyl, aryl, substituted aryl, arylalkyl, substituted arylalkyl, heteroalkyl or $R_{50}C(O)$. In still other embodiments, $R_7$ is alkyl, arylalkyl, heteroalkyl or $R_{50}C(O)$. In still other embodiments, $R_7$ is alkyl, arylalkyl, heteroalkyl or $R_{10}C(O)$. In still other embodiments, $R_1$ is —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_9$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{70}C(O)$, $R_{71}OC(O)$ or $R_{72}NR_{73}C(O)$. In other embodiments, $R_9$ is hydrogen, alkyl, substituted alkyl, aryl, substituted aryl, arylalkyl, substituted arylalkyl, heteroalkyl or $R_{70}C(O)$. In still other embodiments, $R_9$ is hydrogen, alkyl, arylalkyl, heteroalkyl or $R_{70}C(O)$. In still other embodiments, $R_9$ is hydrogen, —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_9$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{70}C(O)$, $R_{71}OC(O)$ or $R_{72}NR_{73}C(O)$. In other embodiments, $R_9$ is alkyl, substituted alkyl, aryl, substituted aryl, arylalkyl, substituted arylalkyl, heteroalkyl or $R_{70}C(O)$. In still other embodiments, $R_9$ is alkyl, arylalkyl, heteroalkyl or $R_{70}C(O)$. In still other embodiments, $R_9$ is —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_{90}$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{100}C(O)$, $R_{101}OC(O)$ or $R_{102}NR_{103}C(O)$. In other embodiments, $R_{90}$ is hydrogen, alkyl, substituted alkyl, aryl, substituted aryl, arylalkyl, substituted arylalkyl, heteroalkyl or $R_{100}C(O)$. In still other embodiments, $R_{90}$ is hydrogen, alkyl, arylalkyl, heteroalkyl or $R_{100}C(O)$. In still other embodiments, $R_{90}$ is hydrogen, —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_{90}$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{90}C(O)$, $R_{91}OC(O)$ or $R_{92}NR_{93}C(O)$. In other embodiments, $R_{90}$ is alkyl, substituted alkyl, aryl, substituted aryl, arylalkyl, substituted arylalkyl, heteroalkyl or $R_{90}C(O)$. In still other embodiments, $R_9$ is alkyl, arylalkyl, heteroalkyl or $R_{90}C(O)$. In still other embodiments, $R_{90}$ is —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_1$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$, $R_{11}OC(O)$ or $R_{12}NR_{13}C(O)$, $R_6$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{30}C(O)$, $R_{31}OC(O)$ or $R_{32}NR_{33}C(O)$, $R_7$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{50}C(O)$, $R_{51}OC(O)$ or $R_{52}NR_{53}C(O)$, $R_9$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{70}C(O)$, $R_{71}OC(O)$ or $R_{72}NR_{73}C(O)$ and $R_{90}$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{100}C(O)$, $R_{101}C(O)$ or $R_{102}NR_{103}C(O)$. In other embodiments, $R_1$ is hydrogen, alkyl, substituted alkyl, aryl, substituted aryl, arylalkyl, substituted arylalkyl, heteroalkyl or $R_{10}C(O)$, $R_6$ is hydrogen, alkyl, substituted alkyl, aryl, substituted aryl, arylalkyl, substituted arylalkyl, heteroalkyl or $R_{30}C(O)$, $R_7$ is hydrogen, alkyl, substituted alkyl, aryl, substituted aryl, arylalkyl, substituted arylalkyl, heteroalkyl or $R_{50}C(O)$, $R_9$ is hydrogen, alkyl, substituted alkyl, aryl, substituted aryl, arylalkyl, substituted arylalkyl, heteroalkyl or $R_{70}C(O)$ and $R_{90}$ is hydrogen, alkyl, substituted alkyl, aryl, substituted aryl, arylalkyl, substituted arylalkyl, heteroalkyl or $R_{100}C(O)$. In still other embodiments, $R_1$ is hydrogen, alkyl, substituted alkyl, aryl, substituted aryl, arylalkyl, substituted arylalkyl, heteroalkyl or $R_{10}C(O)$ and $R_{90}$ is hydrogen, alkyl, substituted alkyl, aryl, substituted aryl, arylalkyl, substituted arylalkyl, heteroalkyl or $R_{100}C$ (O). In still other embodiments, $R_1$ is hydrogen, alkyl, arylalkyl, heteroalkyl or $R_{10}C(O)$, $R_6$ is hydrogen, alkyl, arylalkyl, heteroalkyl or $R_{30}C(O)$, $R_7$ is hydrogen, alkyl, arylalkyl, heteroalkyl or $R_{50}C(O)$, $R_9$ is hydrogen, alkyl, arylalkyl, heteroalkyl or $R_{70}C(O)$ and $R_{90}$ is hydrogen, alkyl, arylalkyl, heteroalkyl or $R_{100}C(O)$. In still other embodiments, $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$, $R_6$ is hydrogen, —$CH_3$, —$CF_3$, —$CH_2Ph$, —$C(O)OCH_3$, —$C(O)OPh$, —$CH_2OCH_3$ or —$CH_2C\equiv CH$, $R_7$ is hydrogen, —$CH_3$, —$CF_3$, —$CH_2Ph$, —$C(O)OCH_3$, —$C(O)OPh$, —$CH_2OCH_3$ or —$CH_2C\equiv CH$, $R_9$ is hydrogen, —$CH_3$, —$CF_3$, —$CH_2Ph$, —$C(O)OCH_3$, —$C(O)OPh$, —$CH_2OCH_3$ or —$CH_2C\equiv CH$ and $R_{90}$ is hydrogen, —$CH_3$, —$CF_3$, —$CH_2Ph$, —$C(O)OCH_3$, —$C(O)OPh$, —$CH_2OCH_3$ or —$CH_2C\equiv CH$.

In some embodiments, $R_1$ is hydrogen, alkyl, arylalkyl, heteroalkyl or $R_{10}C(O)$ and $R_{90}$ is hydrogen, alkyl, arylalkyl, heteroalkyl or $R_{100}C(O)$. In other embodiments, $R_1$ is —$CH_3$, —$CF_3$, —$CH_2Ph$, —$C(O)OCH_3$, —$C(O)OPh$, —$CH_2OCH_3$ or —$CH_2C\equiv CH$ and $R_{90}$ is —$CH_3$, —$CF_3$, —$CH_2Ph$, —$C(O)OCH_3$, —$C(O)OPh$, —$CH_2OCH_3$ or —$CH_2C\equiv CH$. In still other embodiments, $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$ and $R_{90}$ is hydrogen, —$CH_3$, —$CF_3$, —$CH_2Ph$, —$C(O)OCH_3$, —$C(O)OPh$, —$CH_2OCH_3$ or —$CH_2C\equiv CH$. The compound of Claim 2, wherein $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$ and $R_9$ is hydrogen, —$CH_3$, —$CF_3$, —$CH_2Ph$, —$C(O)OCH_3$, —$C(O)OPh$, —$CH_2OCH_3$ or —$CH_2C\equiv CH$ with the proviso that $R_1$ and $R_9$ are not both hydrogen. In still other embodiments, $R_7$ is hydrogen, —$CH_3$, —$CF_3$, —$CH_2Ph$, —$C(O)OCH_3$, —$C(O)OPh$, —$CH_2OCH_3$ or —$CH_2C\equiv CH$ and $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$ with the proviso that $R_7$ and $R_1$ are not both hydrogen. In still other embodiments, $R_6$ is hydrogen, —$CH_3$, —$CF_3$, —$CH_2Ph$, —$C(O)OCH_3$, —$C(O)OPh$, —$CH_2OCH_3$ or —$CH_2C\equiv CH$ and $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$ with the proviso that $R_6$ and $R_1$ are not both hydrogen. In still other embodiments, $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$ and $R_{90}$ is hydrogen, —$CH_3$, —$CF_3$, —$CH_2Ph$, —$C(O)OCH_3$, —$C(O)OPh$, —$CH_2OCH_3$ or —$CH_2C\equiv CH$ with the proviso that $R_{90}$ and $R_1$ are not both hydrogen.

In some embodiments, a compound of Formula (II) is provided:

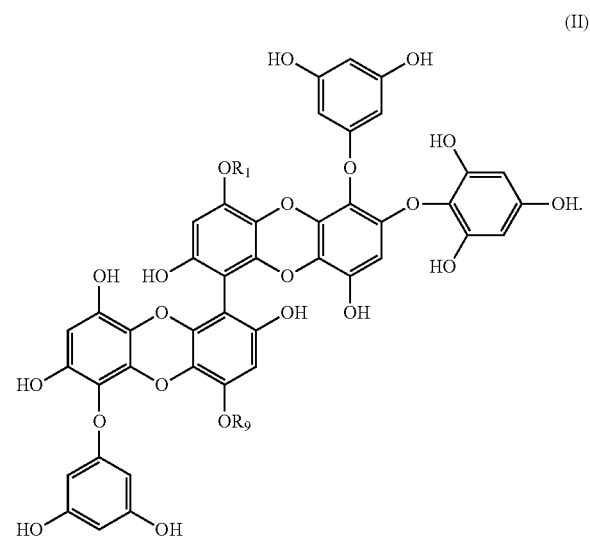

In some embodiments, a compound of Formula (III) is provided:

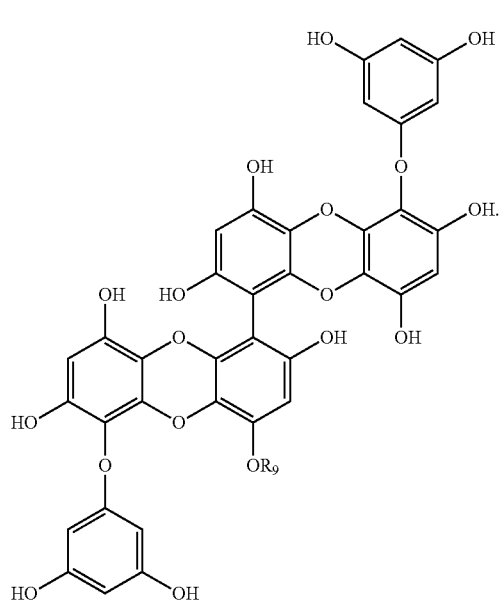
(III)
In some embodiments, a compound of Formula (IV) is provided:
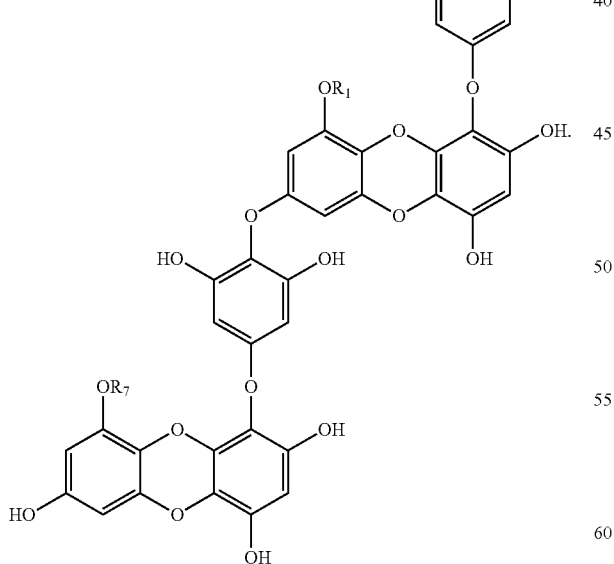
(IV)
In some embodiments, a compound of Formula (V) is provided:
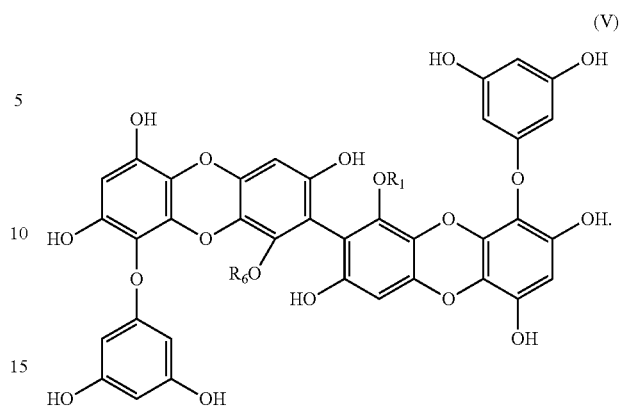
(V)
In some embodiments, a compound of Formula (VI) is provided:
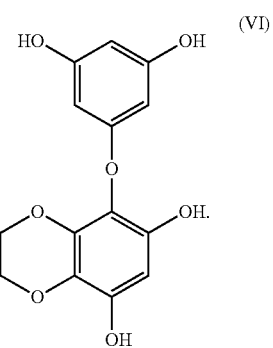
(VI)
In some embodiments, a compound of Formula (VII) is provided:
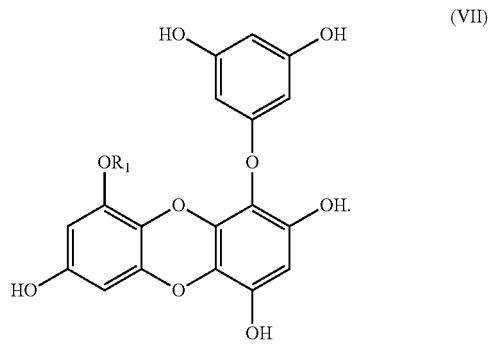
(VII)
In some embodiments, a compound of Formula (VIII) is provided:

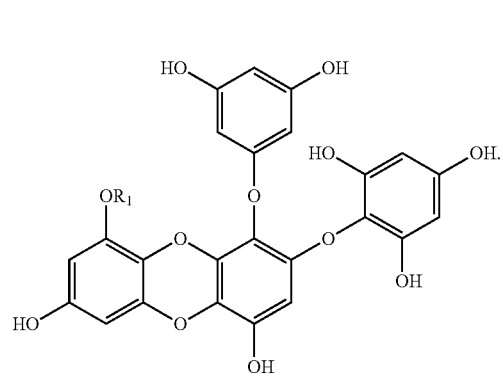

(VIII)

In some embodiments, a compound of Formula (IX) is provided:

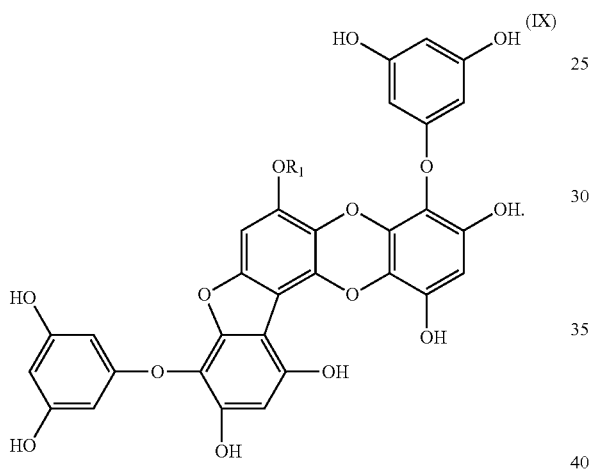

(IX)

In some embodiments, a compound of Formula (X) is provided:

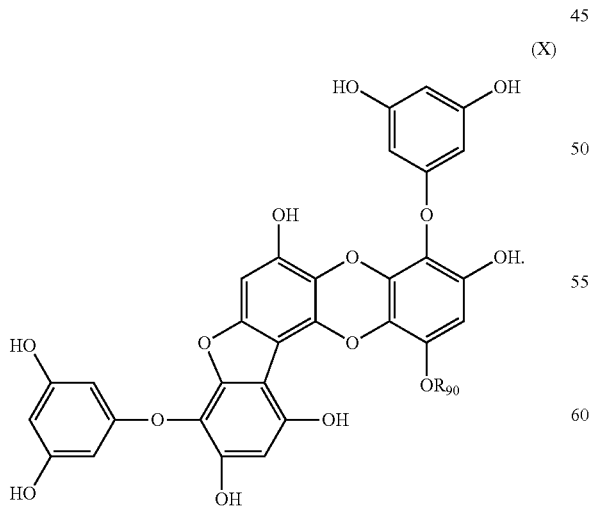

(X)

In some embodiments, a compound of Formula (XI) is provided:

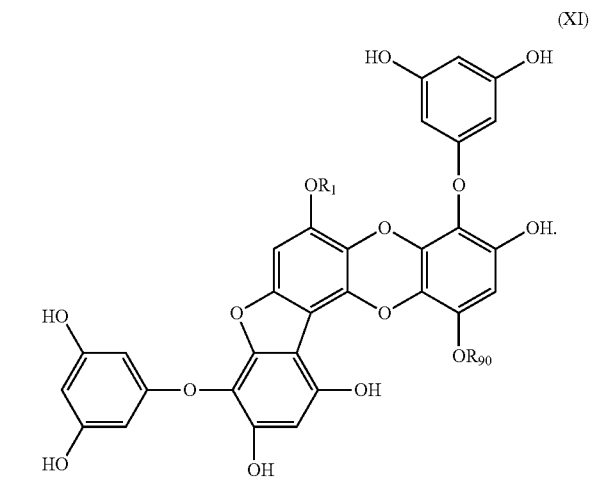

(XI)

In some embodiments, a compound of Formula (XII) is provided:

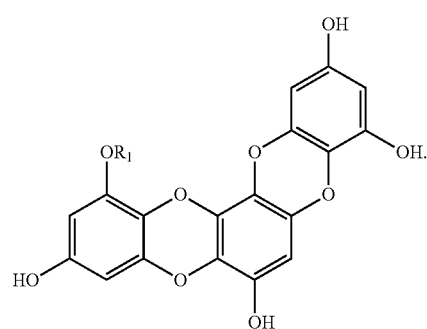

(XII)

In some embodiments, a compound of Formula (XI) is provided:

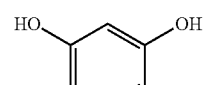

(XIII)

In some of the above embodiments, $R_1$ is —$CH_3$, —$CH_2Ph$, —$C(O)OCH_3$, —$C(O)OPh$, —$CH_2OCH_3$ or —$CH_2C \equiv CH$. In other of the above embodiments, $R_9$ is —$CH_3$, —$CH_2Ph$, —$C(O)OCH_3$, —$C(O)OPh$, —$CH_2OCH_3$ or —$CH_2C \equiv CH$. In still of the other above embodiments, $R_7$ is —$CH_3$, —$CH_2Ph$, —$C(O)OCH_3$, —C(O)OPh, —CH$_2$OCH$_3$ or —CH$_2$C≡CH. In still of the other above embodiments, R$_6$ is —CH$_3$, —CH$_2$Ph, —C(O)OCH$_3$, —C(O)OPh, —CH$_2$OCH$_3$ or —CH$_2$C≡CH. In still of the other above embodiments, R$_{90}$ is —CH$_3$, —CH$_2$Ph, —C(O)OCH$_3$, —C(O)OPh, —CH$_2$OCH$_3$ or —CH$_2$C≡CH.

Exemplary methods for the preparation of compounds of Formula (I) for use in the compositions and methods provided herein are described below. Finally, an important discovery of the present invention is the demonstration herein that regioselective functionalization of dieckol at the 9″ position can take place under carefully controlled conditions. Such regioselective functionalization is unprecedented and offers access to previously unknown 9″ substituted dieckols.

Without wishing to be bound by theory, the functionality depicted in bold may selectively activate the adjacent hydroxyl group in nucleophilic substitution reactions, as depicted for eckol below.

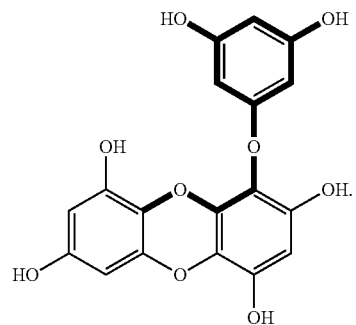

The skilled artisan will appreciate that the above functionality is present in many eckol derivatives and may identify hydroxyls of polyphenol derivatives which may be regioselectively functionalized.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration.

In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically finetuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should produce a serum concentration of active ingredient of from about 0.001 ng/ml to about 50200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once, or may be divided into many smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any subject, specific dosage regimens should be adjusted over time per the individual need and the professional judgment of the person administering or supervising the administration of the compositions and that the concentration ranges set forth herein are exemplary only and are not intended to limit the scope or practice of the claimed compositions.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using cosolvents, such as dimethylsulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon many factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil water emulsions containing suitable quantities of the compounds or derivatives thereof. The therapeutically active compounds and derivatives thereof are, in some embodiments, formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required vehicle. Examples of unit dose forms include ampoules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%100% active ingredient, in one embodiment 0.195%, in another embodiment 0.410%.

In certain embodiments, the compositions are lactose free compositions containing excipients that are well known in the art and are listed, for example, in the U.S. Pharmacopeia (USP) 25NF20 (2002). In general, lactose free compositions contain active ingredients, a binder/filler, and a lubricant in compatible amounts. Particular lactose free dosage forms contain active ingredients, microcrystalline cellulose, pregelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage to determine characteristics such as shelf life or the stability of formulations over time. See, e.g., Jens T. Carstensen, *Drug Stability: Principles & Practice,* 2d. Ed., Marcel Dekker, NY, N.Y., 1995, pp. 37980. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric coated, sugar-coated or filmcoated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are nonaqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of nonaqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semisolid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono or polyalkylene glycol, including, but not limited to, 1,2dimethoxyethane, diglyme, triglyme, tetraglyme, polyethylene glycol350dimethyl ether, polyethylene glycol550dimethyl ether, polyethylene glycol750dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of nontoxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow release or sustained release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylenevinylacetate copolymers, silicone rubbers, polydimethylsiloxanes, silicone carbonate copolymers, hydrophilic polymers such as hydrogels of esters of acrylic and methacrylic acid, collagen, crosslinked polyvinylalcohol and crosslinked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl phydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon several factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein.

All controlled release products have a common goal of improving drug therapy over that achieved by their noncontrolled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRc Crit. Ref Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115138 (1984)). In some embodiments, a controlled release device is introduced into a subject in proximity of the site of inappropriate immune activation or a tumor. Other controlled release systems are discussed in the review by Langer (Science 249:15271533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylenevinylacetate copolymers, silicone rubbers, polydimethylsiloxanes, silicone carbonate copolymers, hydrophilic polymers such as hydrogels of esters of acrylic and methacrylic acid, collagen, crosslinked polyvinylalcohol and crosslinked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest, herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agents. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carriers. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and nonflammable HFA propellants are selected from HFA 134a (1,1,1,2tetrafluoroethane) and HFA 227e (1,1,1,2,3,3,3heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. Because of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01% 10% isotonic solutions, pH about 57.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glyceringelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For nonlimiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue targeted liposomes, such as tumor targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

In human therapeutics, the physician will determine the dosage regimen that is most appropriate according to a preventive or curative treatment and according to the age, weight, stage of the disease and other factors specific to the subject to be treated. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form. The amount of active ingredient in the formulations provided herein, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating symptoms of medical disorders such as, for example, Alzheimer's disease, Parkinson's disease, stroke, microbial infections (i.e., fungal viral, bacterial), circulatory issues (e.g., plasmin inhibition, hypertension, thrombosis, etc.), metabolic disorders (e.g., hypolipidemia, obesity, diabetes, etc.), coronary artery disease, allergic response (e.g., histamine release, IgE receptor response, airway hypersensitiveness, etc.), enzyme activity (e.g., excessive matrix metalloprotease, hyaluronidase, elastase, cholinesterase, tyrosinase activity), arthritis, oral disease, hair and scalp disease, virility issues, skin disease, inflammation (e.g., reduction in NfkB, COX iNOS, treatment of sepsis, etc.), fibromyalgia, cancer and neuralgia are provided herein. In addition, methods of neuroprotection (i.e., reduction of beta amyloid production) and cellular protection (e.g., protection from oxidation and radiation, protection of liver cells) are also provided herein. Furthermore, the eckol derivatives described herein can inhibit enzymes associated with Alzheimer's disease (e.g., acetylcholinesterase, butrylcholinesterase, beta secretase 1, etc.). In practicing the methods, therapeutically effective amounts of the compounds or compositions, described herein, supra, are administered.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with Alzheimer's disease, Parkinson's disease, stroke, microbial infections (i.e., fungal viral, bacterial), circulatory issues (e.g., plasmin inhibition, hypertension, thrombosis, etc.), metabolic disorders (e.g., hypolipidemia, obesity, diabetes, etc.), coronary artery disease, allergic response (e.g., histamine release, IgE receptor response, airway hypersensitiveness, etc.), enzyme activity (e.g., excessive matrix metalloprotease, hyaluronidase, elastase, cholinesterase, tyrosinase activity), arthritis, oral disease, hair and scalp disease, virility issues, skin disease, inflammation (e.g., reduction in NfkB, COX iNOS, etc.), fibromyalgia, cancer and neuralgia. In addition, other therapeutic agents including those known for neuroprotection (i.e., reduction of beta amyloid production) and Cellular protection (e.g., protection from oxidation and radiation, protection of liver cells) may be co-administered with the compounds and pharmaceutical compositions described herein.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The following examples are provided thr illustrative purposes only and are not intended to limit the scope of the invention.

EXAMPLES

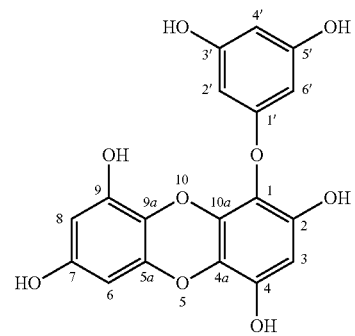

-continued

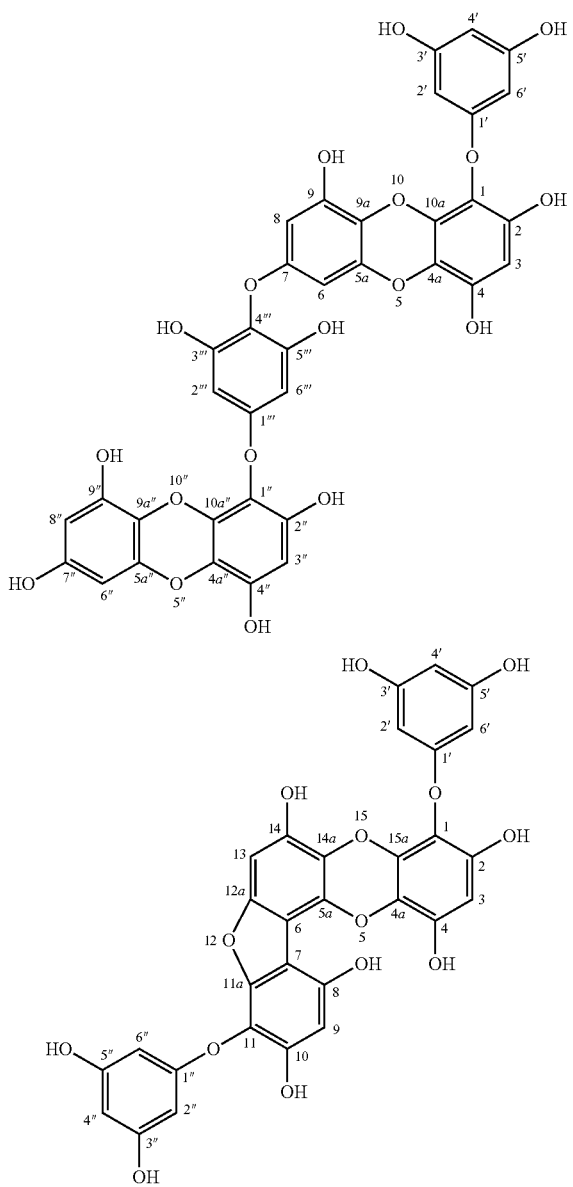

Shown above are numbering schemes for eckol, dieckol and phlorofucofuroeckol A, respectively, which will assist those of skill in the art in understanding the NMR spectra reported below.

All reactions were carried out under nitrogen or argon atmosphere. DMF was purchased from Sigma Aldrich Co. (St. Louis, Mo.). Acetone was dehydrated using 4-Å molecular sieves. $^1$H NMR (600 MHz) and $^{13}$C NMR (150 MHz) were acquired using DMSO-$d_6$. Chemical shifts were referenced to the residual solvent peaks ($\delta_H$ 2.50 and $\delta_C$ 39.5 for DMSO-$d_6$). All coupling constants, J, are reported in hertz (Hz). Column chromatography was performed on silica gel 60, 70-230 mesh. Analytical thin-layer chromatography (TLC) was performed using Merck Kieselgel 60 F254 precoated plates (0.25 mm) with a fluorescent indicator and visualized with UV light (254 and 365 nm).

Example 1: Analysis of Dieckol

TLC $R_f$=0.18 (Chloroform:Methanol:Water=60:30:4); H-NMR (600 MHz, DMSO-$d_6$) δ 9.67 (s, 1H, $C_9$—OH), 9.57 (s, 1H, $C_9$—OH), 9.47 (s, 1H, $C_{4'''}$—OH), 9.42 (s, 1H, $C_{4'}$—OH), 9.32 (s, 2H, $C_{3''',5'''}$—OH), 9.25 (s, 1H, $C_{2''}$—OH), 9.20 (s, 1H, $C_{2'}$—OH), 9.19 (s, 1H, $C_{7''}$—OH), 9.13 (s, 2H, $C_{3',5'}$—OH), 6.16 (s, 1H, $C_{3'''}$—H), 6.14 (s, 1H, $C_3$—H), 6.02 (d, J=2.85 Hz, 1H, $C_8$—H), 5.99 (d, J=2.74 Hz, 1H, $C_{8''}$—H), 5.95 (s, 2H, $C_{2''',6'''}$—H), 5.82 (d, J=2.83 Hz, 1H, $C_6$—H), 5.81 (d, J=2.72 Hz, 1H, $C_{6''}$—H), 5.80 (t, J=2.09 Hz, 1H, $C_{4'}$—H), 5.72 (d, J=2.09 Hz, 2H, $C_{2',6'}$—H); $^{13}$C-NMR (600 MHz, 154.63 (s, 1C, 7-C), 153.47 (s, 1C, 7''-C), 151.55 (s, 2C, 3''',5'''-C), 146.49 (s, 1C, 2-C), 146.45 (s, 1C, 9''-C), 146.36 (s, 1C, 9-C), 146.31 (s, 1C, 2''-C), 142.99 (s, 1C, 5a''-C), 142.80 (s, 1C, 5a-C), 142.37 (s, 1C, 4''-C), 142.27 (s, 1C, 4-C), 137.63 (s, 1C, 10a''-C), 137.46 (s, 1C, 10a-C), 124.62 (s, 1C, 4'''-C), 124.42 (s, 1C, 9a-C), 123.63 (s, 1C, 4a''-C), 123.55 (s, 1C, 4a-C), 122.99 (s, 1C, 9a''-C), 122.68 (s, 1C, 1''-C), 122.61 (s, 1C, 1-C), 98.90 (s, 1C, 8''-C), 98.75 (s, 1C, 3-C), 98.63 (s, 1C, 3''-C), 98.46 (s, 1C, 8-C), 96.63 (s, 1C, 4'-C), 94.90 (s, 2C, 2''',6'''-C), 94.27 (s, 1C, 6''-C), 94.05 (s, 2C, 2',6'-C), 93.94 (s, 1C, 6-C).

Example 2: Preparation of 9'''-O-Methyl Dieckol

Dry acetone (100 mL) was added to a mixture of dieckol (300 mg, 0.404 mmol) and anhydrous potassium carbonate (55.84 mg, 0.404 mmol) in a round-bottom flask under $N_2$ atmosphere. Dimethyl sulfate (38.32 μL, 0.404 mmol) was added in small portions after stirring for 10 minutes. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:9) to afford 9'''-methoxy dieckol (195.5 mg, 64%) as a pale-yellow powder. TLC $R_f$=0.35 (Chloroform:Methanol:Water=60:30:4); $^1$H-NMR (600 MHz, DMSO-$d_6$) δ 9.66 (s, 1H, $C_9$—OH), 9.53 (s, 1H, $C_{4'}$—OH), 9.42 (s, 2H, $C_{4,7''}$—OH), 9.33 (s, 2H, $C_{3'',5''}$—OH), 9.30 (s, 1H, $C_{2''}$—OH), 9.20 (s, 1H, $C_2$—OH), 9.13 (s, 2H, $C_{3''',5'''}$—OH), 6.19 (s, 1H, $C_{3'''}$—H), 6.15 (s, 1H, $C_3$—H), 6.09 (d, J=2.69 Hz, 1H, $C_{8'''}$—H), 6.04 (d, J=2.86 Hz, 1H, $C_8$—H), 5.98 (d, J=2.60 Hz, 1H, $C_{6''}$—H), 5.96 (s, 2H, $C_{2'',6''}$—H), 5.81 (t, J=2.10 Hz, 1H, $C_{4'}$—H), 5.79 (d, J=2.84 Hz, 1H, $C_6$—H), 5.73 (d, J=2.10 Hz, 2H, $C_{2',6'}$—H), 3.66 (s, 3H, $C_{9''}$—OCH$_3$); $^{13}$C-NMR (600 MHz, DMSO-$d_6$) δ 160.70 (s, 1C, 1'-C), 159.21 (s, 2C, 3',5'-C), 156.28 (s, 1C, 1'''-C), 154.63 (s, 1C, 7-C), 153.85 (s, 1C, 7''-C), 151.58 (s, 2C, 3''',5'''-C), 148.66 (s, 1C, 9''-C), 146.49 (s, 1C, 2-C), 146.46 (s, 1C, 2''-C), 146.36 (s, 1C, 9'-C), 142.81 (s, 1C, 5a-C), 142.75 (s, 1C, 5a''-C), 142.42 (s, 1C, 4''-C), 142.29 (s, 1C, 4-C), 137.47 (s, 1C, 10a-C), 137.43 (s, 1C, 10a''-C), 124.68 (s, 1C, 4'''-C), 124.47 (s, 1C, 9a-C), 123.85 (s, 1C, 9a''-C), 123.56 (s, 2C, 4a,4a''-C), 122.72 (s, 1C, 1''-C), 122.62 (s, 1C, 1-C), 98.85 (s, 1C, 3''-C), 98.75 (s, 1C, 3-C), 98.61 (s, 1C, 8-C), 96.63 (s, 1C, 4'-C), 96.39 (s, 1C, 8''-C), 95.64 (s, 1C, 6''-C), 94.91 (s, 2C, 2''',6'''-C), 94.07 (s, 2C, 2',6'-C), 93.81 (s, 1C, 6-C), 56.59 (s, 1C, 9''-COC).

Example 3: Preparation of 9'''-O-Benzyl Dieckol

Dry acetone (100 mL) was added to a mixture of dieckol (300 mg, 0.404 mmol) and anhydrous potassium carbonate (55.84 mg, 0.404 mmol) in a round-bottom flask under $N_2$ atmosphere. Benzyl bromide (48.05 μL, 0.404 mmol) was added in small portions after stirring for 10 minutes. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:9) to afford 9‘ ’-benzyloxy dieckol (222.02 mg, 66%) as a pale yellow powder. TLC $R_f$=0.42 (Chloroform:Methanol:Water=60:30:4); $^1$H-NMR (600 MHz, DMSO-$d_6$) δ 9.63 (s, 1H, $C_9$—OH), 9.56 (s, 1H, $C_{4''}$—OH), 9.42 (s, 1H, $C_4$—OH), 9.41 (s, 1H, $C_{7'}$—OH), 9.35 (s, 2H, $C_{3''',5'''}$—OH), 9.33 (s, 1H, $C_{2''}$—OH), 9.18 (s, 1H, $C_2$—OH), 9.12 (s, 2H, $C_{3''',5'''}$—OH), 7.33 (dd, J=7.54 Hz, 2H, $C_{9''}$—OCH$_2$C(CH)$_2$(CH)$_2$), 7.27 (t, J=7.31 Hz, 1H, $C_{9''}$—OCH$_2$C(CH)$_2$(CH)$_2$CH), 7.24 (d, J=7.28 Hz, 2H, $C_{9''}$—OCH$_2$C(CH)$_2$), 6.21 (s, 1H, $C_{3''}$—H), 6.15 (d, 1H, J=2.69 Hz, $C_{8''}$—H), 6.14 (s, 1H, $C_3$—H), 6.04 (d, J=2.87 Hz, 1H, $C_8$—H), 6.01 (s, 1H, $C_{6''}$—H), 6.00 (s, 2H, $C_{2'',6'''}$—H), 5.80 (t, J=2.07 Hz, 1H, $C_{4'}$—H), 5.78 (d, J=2.84 Hz, 1H, $C_6$—H), 5.72 (d, J=2.09 Hz, 2H, $C_{2',6'}$—H), 4.97 (s, 2H, $C_{9''}$—CH$_2$); $^{13}$C-NMR (600 MHz, DMSO-$d_6$) δ 160.69 (s, 1C, 1'-C), 159.20 (s, 2C, 3',5'-C), 156.24 (s, 1C, 1'''-C), 154.62 (s, 1C, 7-C), 153.73 (s, 1C, 7''-C), 151.65 (s, 2C, 3''',5'''-C), 147.43 (s, 1C, 9''-C), 146.60 (s, 1C, 2''-C), 146.46 (s, 1C, 2-C), 146.32 (s, 1C, 9-C), 142.85 (s, 1C, 5a''-C), 142.76 (s, 1C, 5a-C), 142.54 (s, 1C, 4''-C), 142.28 (s, 1C, 4-C), 137.43 (d, J=3.75 Hz, 1C, 10a-C), 137.23 (s, 1C, 10a''-C), 128.74 (s, 2C, 9''-COCH$_2$C(CH)$_2$(CH)$_2$), 127.94 (s, 1C, 9''-COCH$_2$C(CH)$_2$(CH)$_2$CH), 127.28 (s, 2C, 9''-COCH$_2$C), 124.69 (s, 1C, 4'''-C), 124.62 (s, 1C, 9a''-C), 124.45 (s, 1C, 9a'-C), 123.63 (s, 1C, 4a''-C), 123.55 (s, 1C, 4a-C), 122.60 (s, 1C, 1-C), 122.39 (s, 1C, 1''-C), 98.83 (s, 1C, 3''-C), 98.74 (s, 1C, 3-C), 98.71 (s, 1C, 8-C), 98.43 (s, 1C, 8''-C), 96.63 (s, 1C, 4'-C), 96.25 (s, 1C, 6''-C), 94.52 (s, 2C, 2''',6'''-C), 94.06 (s, 2C, 2',6'-C), 93.85 (s, 1C, 6-C), 70.59 (s, 1C, 9''-COC).

Example 4: Preparation of 9''-O-Acetyl Dieckol

Dry acetone (100 mL) and pyridine (32.55 μL (0.404 mmol) was added to dieckol (300 mg, 0.404 mmol) in a round-bottom flask under N$_2$ atmosphere. Acetyl chloride (28.73 μL, 0.404 mmol) was added in small portions after stirring for 10 minutes. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:9) to afford 9''-acetoxy dieckol (190.2 mg, 60%) as a pale yellow powder. TLC $R_f$=0.34 (Chloroform:Methanol:Water=60:30:4); $^1$H-NMR (600 MHz, DMSO-$d_6$) δ 9.67 (s, 1H, $C_{7'}$—OH), 9.65 (s, 1H, $C_{4''}$—OH), 9.63 (s, 1H, $C_9$—OH), 9.42 (s, 1H, $C_4$—OH), 9.38 (s, 1H, $C_{2''}$—OH), 9.31 (s, 2H, $C_{3''',5'''}$—OH), 9.19 (s, 1H, $C_2$—OH), 9.12 (s, 2H, $C_{3''',5'''}$—OH), 6.28 (d, J=2.72 Hz, 1H, $C_{6''}$—H), 6.22 (s, 1H, $C_{3''}$—H), 6.16 (d, J=2.75 Hz, 1H, $C_8$—H), 6.15 (s, 1H, $C_3$—H), 6.06 (d, J=2.83 Hz, 1H, $C_8$—H), 5.92 (s, 2H, $C_{2'',6'''}$—H), 5.81 (d, J=2.86 Hz, 1H, $C_6$—H), 5.80 (d, J=2.07 Hz, 1H, $C_{4'}$—H), 5.73 (d, J=2.04 Hz, 2H, $C_{2',6'}$—H), 2.02 (s, 3H, $C_9$''-OCOCH$_3$); $^{13}$C-NMR (600 MHz, DMSO-$d_6$) δ 160.70 (s, 1C, 1'-C), 159.20 (s, 2C, 3',5'-C), 156.12 (s, 1C, 1'''-C), 154.68 (s, 1C, 7-C), 153.52 (s, 1C, 7''-C), 151.66 (s, 2C, 3''',5'''-C), 146.85 (s, 1C, 2''-C), 146.46 (s, 1C, 2-C), 146.33 (s, 1C, 9-C), 142.99 (s, 1C, 5a''-C), 142.84 (s, 1C, 5a-C), 142.61 (s, 1C, 4''-C), 142.32 (s, 1C, 4-C), 139.05 (s, 1C, 9''-c), 137.51 (s, 1C, 10a-C), 136.71 (s, 1C, 10a''-C), 126.36 (s, 1C, 9a''-C), 124.63 (s, 1C, 4'''-C), 124.52 (s, 1C, 9a-C), 123.58 (s, 1C, 4a-C), 123.56 (s, 1C, 4a''-C), 122.61 (s, 1C, 1-C), 122.30 (s, 1C, 1''-C), 104.91 (s, 1C, 8''-C), 101.01 (s, 1C, 6''-C), 99.04 (s, 1C, 3''-C), 98.81 (s, 1C, 8-C), 98.73 (s, 1C, 3-C), 96.63 (s, 1C, 4'-C), 94.32 (s, 2C, 2'''.6'''-C), 94.07 (s, 2C, 2',6'-C), 93.72 (s, 1C, 6-C), 21.21 (s, 1C, 9''-COC), 20.18 (s, 1C, 9''-COCOC).

Example 5: Preparation of 9''-O-Benzoyl Dieckol

Dry acetone (100 mL) and pyridine (32.55 μL (0.404 mmol) was added to dieckol (300 mg, 0.404 mmol) in a round-bottom flask under N$_2$ atmosphere. Benzoyl chloride (46.94 μL, 0.404 mmol) was added in small portions after stirring for 10 minutes. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:9) to afford 9''-benzoyloxy dieckol (215.5 mg, 63%) as a pale yellow powder. TLC $R_f$=0.40 (Chloroform:Methanol:Water=60:30:4); $^1$H-NMR (600 MHz, DMSO-$d_6$) (9.76 (s, 1H, $C_{7'}$—OH), 9.67 (s, 1H, $C_{4''}$—OH), 9.65 (s, 1H, $C_9$—OH), 9.41 (s, 1H, $C_4$—OH), 9.34 (s, 1H, $C_{2''}$—OH), 9.19 (s, 1H, $C_2$—OH), 9.17 (s, 2H, $C_{3''',5'''}$—OH), 9.12 (s, 2H, $C_{3''',5'''}$—OH), 7.81 (dd, $J_1$=8.24 Hz, $J_2$=1.23 Hz, 2H, $C_9$''-OCOC(CH)$_2$), 7.69 (tt, J=7.47 Hz, $J_2$=1.24 Hz, 1H, $C_{9''}$—OCOC(CH)$_2$(CH)$_2$CH), 7.50 (t, J=7.59 Hz, 2H, $C_{9''}$—OCOC(CH)$_2$(CH)$_2$), 6.38 (d, J=2.75 Hz, 1H, $C_{8''}$—H), 6.35 (d, J=2.71 Hz, 1H, $C_{6''}$—H), 6.23 (s, 1H, $C_{3''}$—H), 6.15 (s, 1H, $C_{3'}$—H), 6.06 (d, J=2.87 Hz, 1H, $C_8$—H), 5.80 (t, J=2.08 Hz, 1H, $C_{4'}$—H), 5.78 (d, J=2.82 Hz, 1H, $C_6$—H), 5.73 (d, J=2.09 Hz, 2H, $C_{2',6'}$—H), 5.70 (s, 2H, $C_{2'',6'''}$—H); $^{13}$C-NMR (600 MHz, DMSO-$d_6$) δ 164.01 (s, 1C), 160.70 (s, 1C, 1'-C), 159.20 (s, 2C, 3',5'-C), 155.79 (s, 1C, 1'''-C), 154.66 (s, 1C, 7-C), 153.55 (s, 1C, 7''-C), 151.41 (s, 2C, 3''',5'''-C), 146.76 (s, 1C, –2''C), 146.46 (s, 1C, 2-C), 146.33 (s, 1C, 9-C), 143.16 (s, 1C, 5a''-C), 142.80 (s, 1C, 5a-C), 142.65 (s, 1C, 4''-C), 142.31 (s, 1C, 4-C), 139.07 (s, 1C, 9''-C), 137.48 (s, 1C, 10a-C), 137.05 (s, 1C, 10a''-C), 130.02 (s, 2C, 9''-COCOC(CH)$_2$), 129.19 (s, 2C, 9''-COCOC(CH)$_2$(CH)$_2$), 128.54 (s, 1C, 9''-COCOC(CH)$_2$(CH)$_2$CH), 126.47 (s, 1C, 9a''-C), 124.61 (s, 1C, 4'''-C), 124.50 (s, 1C, 9a-C), 123.58 (s, 1C, 4a-C), 123.52 (s, 1C, 4a''-C), 122.60 (s, 1C, 1-C), 122.14 (s, 1C, 1''-C), 105.03 (s, 1C, 8''-C), 101.13 (s, 1C, 6''-C), 99.21 (s, 1C, 3''-C), 98.85 (s, 1C, 8-C), 98.73 (s, 1C, 3-C), 96.62 (s, 1C, 4'-C), 94.20 (s, 2C, 2''',6'''-C), 94.07 (s, 2C, 2',6'-C), 93.83 (s, 1C, 6-C).

Example 7: Preparation of 9''-O-(Methoxy-methyl)-Dieckol

DMF (70 mL) was added to a mixture of dieckol (200 mg, 0.269 mmol) and anhydrous potassium carbonate (55.84 mg, 0.269 mmol) in a round-bottom flask under N$_2$ atmosphere. Chloromethyl methyl ether (20.46 μL, 0.269 mmol) was added in small portions after stirring for 10 minutes. The reaction mixture was stirred at room temperature for 16 h and diluted with EtOAc; washed with 1% aqueous HCl, water and saturated aqueous NaCl; dried over MgSO$_4$; and concentrated in vacuo. The crude compound was purified by column chromatography (methanol:chloroform=1:9) to afford 9''-(Methoxy methoxy) dieckol (120.6 mg, 57%) as a pale yellow powder. TLC $R_f$=0.34 (Chloroform:Water=60:30:4); $^1$H-NMR (600 MHz, DMSO-$d_6$) δ 9.68 (s, 1H, $C_9$—OH), 9.59 (s, 1H, $C_{4''}$—OH), 9.46 (s, 1H, $C_{7''}$—OH), 9.45 (s, 1H, $C_4$—OH), 9.35 (s, 1H, $C_{2''}$—OH), 9.34 (s, 2H, $C_{3''',5'''}$—OH), 9.22 (s, 1H, $C_2$—OH), 9.14 (s, 2H, $C_{3''',5'''}$—OH), 6.20 (s, 1H, 3''-H), 6.18 (d, J=2.69 Hz, 1H, $C_8$''—H), 6.14 (s, 1H, $C_3$—H), 6.07 (d, J=2.66 Hz, 1H, $C_{6''}$—H), 6.03 (d, J=2.85 Hz, 1H, $C_8$—H), 5.95 (s, 2H, $C_{2'',6'''}$—H), 5.80 (t, J=2.04 Hz, 1H, $C_{4'}$—H), 5.76 (d, J=2.81 Hz, 1H, $C_6$—H), 5.72 (d, J=2.08 Hz, 2H, $C_{2',6'}$—H), 4.94 (s, 2H, $C_{9''}$—OCH$_2$), 3.25 (s, 3H, $C_{9''}$—OCH$_2$OCH$_3$); $^{13}$C-NMR (600 MHz, DMSO-$d_6$) δ 160.69 (s, 1C, 1'-C), 159.20 (s, 2C, 3',5'-C), 156.23 (s, 1C, 1'''-C), 154.60 (s, 1C, 7-C), 153.63 (s, 1C, 7''-C), 151.60 (s, 2C, 3''',5'''-C), 146.58 (s, 1C, 2''-C), 146.47 (s, 1C, 2-C), 146.34 (s, 1C, 9-C), 145.60 (s, 1C, 9''-C), 142.98 (s, 1C, 5a''-C), 142.79 (s, 1C, 5a-C), 142.49 (s, 1C, 4''-C), 142.29 (s, 1C, 4-C), 137.47 (s, 1C, 10a-C), 137.24 (s, 1C, 10a''-C), 125.55 (s, 1C, 9a''-C), 124.66 (s, 1C, 4'''-C), 124.48 (s, 1C, 9a-C), 123.57 (s, 1C, 4a''-C), 123.55 (s, 1C, 4a-C), 122.63 (s, 1C, 1''-C), 122.61 (s, 1C, 1-C), 101.08 (s, 1C, 8"-C), 98.89 (s, 1C, 3"-C), 98.73 (s, 1C, 3-C), 98.71 (s, 1C, 8-C), 97.65 (s, 1C, 6"-C), 96.62 (s, 1C, 4'-C), 95.93 (s, 1C, 9"-COCH$_2$), 94.74 (s, 2C, 2'",6'"-C), 94.06 (s, 2C, 2',6'-C), 93.73 (s, 1C, 6-C), 56.06 (s, 1C, 9"-COCH$_2$CH$_3$).

Example 8: Preparation of 9"-O-Propargyl Dieckol

DMF (30 mL) was added to a mixture of dieckol (100 mg, 0.135 mmol) and anhydrous potassium carbonate (18.61 mg, 0.135 mmol) in a round-bottom flask under N$_2$ atmosphere. Propargyl bromide (10.20 μL, 0.135 mmol) was added in small portions after stirring for 10 minutes. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:9) to afford 9"-propargyloxy dieckol (63.2 mg, 60%) as a pale yellow powder. TLC R$_f$=0.43 (Chloroform:Methanol:Water=60:30:4); $^1$H-NMR (600 MHz, DMSO-d$_6$) δ 9.65 (s, 1H, C$_9$—OH), 9.56 (s, 1H, C$_{4"}$—OH), 9.49 (s, 1H, C$_{7'}$—OH), 9.43 (s, 1H, C$_4$—OH), 9.32 (s, 1H, C$_2$—OH), 9.32 (s, 2H, C$_{3",5"}$—OH), 9.19 (s, 1H, C$_2$—OH), 9.12 (s, 2H, C$_{3'",5'"}$—OH), 6.20 (s, 1H, C$_{3"}$—H), 6.18 (d, J=2.65 Hz, 1H, C$_{8"}$—H), 6.14 (s, 1H, C$_3$—H), 6.04 (d, J=2.61 Hz, 1H, C$_{6"}$—H), 6.03 (s, 1H, C$_8$—H), 5.96 (s, 2H, C$_{2",6"}$—H), 5.80 (t, J=2.06 Hz, 1H, C$_{4'}$—H), 5.79 (d, J=2.85 Hz, 1H, C$_6$—H), 5.72 (d, J=2.07 Hz, 2H, C$_{2',6'}$—H), 4.66 (d, J=2.43 Hz, 2H, C$_{9"}$—OCH$_2$), 3.55 (t, J=2.36 Hz, 1H, C$_{9"}$—OCH$_2$C≡CH); $^{13}$C-NMR (600 MHz, DMSO-d$_6$) δ 160.69 (s, 1C, 1'-C), 159.20 (s, 2C, 3',5'-C), 156.24 (s, 1C, 1'"-C), 154.60 (s, 1C, 7-C), 153.57 (s, 1C, 7"-C), 151.60 (s, 2C, 3'",5'"-C), 146.52 (s, 1C, 2"-C), 146.47 (s, 1C, 2-C), 146.34 (s, 1C, 9-C), 146.24 (s, 1C, 9"-C), 142.89 (s, 1C, 5a"-C), 142.79 (s, 1C, 5a-C), 142.44 (s, 1C, 4"-C), 142.27 (s, 1C, 4-C), 137.46 (s, 1C, 10a-C), 137.24 (s, 1C, 10a"-C), 124.70 (s, 1C, 4'"-C), 124.49 (s, 1C, 9a-C), 124.44 (s, 1C, 9a"-C), 123.54 (s, 1C, 4a-C), 123.50 (s, 1C, 4a"-C), 122.72 (s, 1C, 1"-C), 122.61 (s, 1C, 1-C), 98.94 (s, 1C, 3"-C), 98.72 (s, 1C, 3-C), 98.66 (s, 1C, 8"-C), 98.59 (s, 1C, 8-C), 96.77 (s, 1C, 4'-C), 96.62 (s, 1C, 6"-C), 94.87 (s, 2C, 2'",6'"''-C), 94.05 (s, 2C, 2',6'-C), 93.82 (s, 1C, 6-C), 57.01 (s, 1C, 9"-COCH$_2$).

Example 9: Analysis of Phlorofucofuroeckol A

TLC R$_f$=0.34 (Chloroform:Methanol:Water=60:30:4); $^1$H-NMR (600 MHz, DMSO-d$_6$) (10.13 (s, 1H), 9.86 (s, 1H), 9.84 (s, 1H), 9.43 (s, 1H), 9.20 (s, 2H), 9.17 (s, 2H), 8.21 (s, 1H), 6.72 (s, 1H), 6.44 (s, 1H), 6.30 (s, 1H), 5.84 (s, 2H), 5.77 (s, 2H), 5.73 (s, 2H); $^{13}$C-NMR (600 MHz, DMSO-d$_6$) (160.64 (1C), 160.37 (1C), 159.43 (2C), 159.25 (2C), 151.24 (1C), 150.77 (1C), 149.90 (1C), 147.35 (1C), 146.90 (1C), 145.17 (1C), 142.42 (1C), 137.25 (1C), 134.37 (1C), 126.76 (1C), 123.04 (1C), 122.88 (1C), 120.53 (1C), 103.82 (1C), 103.65 (1C), 99.52 (1C), 98.70 (1C), 96.89 (1C), 96.77 (1C), 95.22 (1C), 94.15 (2C), 93.91 (2C).

Example 10: Preparation of 4,14-O,O-Dimethyl Phlorofucofuroeckol-A

To the mixture of Phlorofucofuroeckol-A (200 mg, 0.332 mmol) and anhydrous potassium carbonate (87.18 mg, 0.631 mmol) in a round-bottom flask under N$_2$ atmosphere, 50 mL of dry acetone was added. After stirring for 10 minutes dimethyl sulfate (59.82 μL, 0.631 mmol) was added in small portions. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:50) to afford 4,14-O, O-dimethyl PFF-A (92.2 mg, 44%) as a pale yellow powder.

TLC R$_f$=0.53 (Chloroform:Methanol:Water=60:30:4); $^1$H-NMR (600 MHz, DMSO-d$_6$) 9.94 (s, 1H), 9.68 (s, 1H), 9.24 (s, 2H), 9.23 (s, 2H), 8.42 (s, 1H), 7.11 (s, 1H), 6.47 (s, 1H), 6.40 (s, 1H), 5.85 (t, J=2.00 Hz, 1H), 5.84 (t, J=2.00 Hz, 1H), 5.78 (d, J=2.02 Hz, 2H), 5.74 (d, J=2.02 Hz, 2H), 3.86 (s, 3H), 3.73 (s, 3H); $^{13}$C-NMR (600 MHz, DMSO-d$_6$) δ 160.44 (1C), 160.41 (1C), 159.43 (2C), 159.30 (2C), 151.51 (1C), 151.07 (1C), 150.17 (1C), 147.52 (1C), 147.48 (1C), 147.04 (1C), 144.57 (1C), 136.96 (1C), 134.25 (1C), 127.36 (1C), 124.25 (1C), 124.04 (1C), 120.50 (1C), 105.06 (1C), 103.73 (1C), 99.58 (1C), 96.99 (1C), 96.93 (1C), 96.69 (1C), 94.30 (2C), 93.98 (2C), 57.33 (1C), 57.16 (1C).

Example 11: Preparation of 4,14-O,O-Diacetyl Phlorofucofuroeckol-A

To phlorofucofuroeckol-A (200 mg, 0.332 mmol) in a round-bottom flask under N$_2$ atmosphere was added 50.81 μL of pyridine (0.631 mmol) and 50 mL of dry acetone. After stirring for 10 minutes acetyl chloride (44.84 μL, 0.631 mmol) in small portions was added. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:50) to afford 4,14-O, O-diacetyl PFF-A (91.1 mg, 40%) as a pale yellow powder.

TLC R$_f$=0.59 (Chloroform:Methanol:Water=60:30:4); $^1$H-NMR (600 MHz, DMSO-d$_6$) (10.01 (s, 1H), 9.90 (s, 1H), 9.73 (s, 1H), 9.27 (s, 2H), 9.17 (s, 2H), 7.15 (s, 1H), 6.55 (s, 1H), 6.45 (s, 1H), 5.87 (t, J=2.07 Hz, 1H), 5.82 (t, J=2.09 Hz, 1H), 5.76 (d, J=2.07 Hz, 2H), 5.72 (d, J=2.09 Hz, 2H), 2.39 (s, 3H), 2.02 (s, 3H); $^{13}$C-NMR (600 MHz, DMSO-d$_6$) (168.71 (1C), 168.35 (1C), 160.39 (1C), 159.72 (1C), 159.48 (2C), 159.42 (2C), 151.59 (1C), 151.24 (1C), 150.91 (1C), 149.80 (1C), 147.38 (1C), 136.73 (1C), 136.33 (1C), 135.27 (1C), 134.91 (1C), 129.91 (1C), 127.82 (1C), 124.34 (1C), 119.74 (1C), 110.64 (1C), 105.58 (1C), 103.58 (1C), 101.87 (1C), 99.83 (1C), 97.08 (1C), 96.89 (1C), 93.89 (2C), 93.62 (2C), 21.13 (1C), 20.05 (1C).

Example 12: Preparation of 4,14-O,O-Dibenzyl Phlorofucofuroeckol-A

To a mixture of phlorofucofuroeckol-A (200 mg, 0.332 mmol) and anhydrous potassium carbonate (87.18 mg, 0.631 mmol) in a round-bottom flask under N$_2$ atmosphere 50 mL of dry acetone was added. After stirring for 10 minutes benzyl bromide (75.02 μL, 0.631 mmol) in small portions was added. The reaction mixture was stirred at room temperature for 16 h and diluted with EtOAc; washed with 1% aqueous HCl, water, and saturated aqueous NaCl; dried over MgSO$_4$; and concentrated in vacuo. The crude compound was purified by column chromatography (methanol:chloroform=1:50) to afford 4,14-O, O-dibenzyl PFF-A (106.5 mg, 41%) as a pale yellow powder.

TLC R$_f$=0.63 (Chloroform:Methanol:Water=60:30:4); $^1$H-NMR (600 MHz, DMSO-d$_6$) (9.92 (s, 1H), 9.63 (s, 1H), 9.25 (s, 2H), 9.21 (s, 2H), 8.43 (s, 1H), 7.53 (d, J=6.97 Hz, 2H), 7.43 (t, J=7.50 Hz, 2H), 7.36 (tt, J$_1$=7.38 Hz, J$_2$=1.28 Hz, 1H), 7.33 (t, J=7.50 Hz, 2H), 7.26 (tt, J$_1$=7.38 Hz, J$_2$=1.28 Hz, 1H), 7.22 (d, J=6.97 Hz, 2H), 7.19 (s, 1H), 6.44 (s, 1H), 6.43 (s, 1H), 5.88 (t, J=2.07 Hz, 1H), 5.84 (t, J=2.07 Hz, 1H), 5.82 (d, J=2.07 Hz, 2H), 5.73 (d, J=2.07 Hz, 2H), 5.26 (s, 2H), 5.05 (s, 2H); $^{13}$C-NMR (600 MHz, DMSO-d$_6$) δ 160.40 (1C), 160.31 (1C), 159.42 (2C), 159.39 (2C), 151.34 (1C), 151.16 (1C), 150.24 (1C), 147.66 (1C), 147.46 (1C), 145.52 (1C), 143.47 (1C), 137.11 (1C), 137.04 (1C), 136.92 (1C), 134.45 (1C), 128.90 (2C), 128.79 (2C), 128.72

(1C), 128.40 (1C), 128.04 (2C), 127.97 (1C), 127.28 (2C), 124.38 (1C), 124.15 (1C), 105.67 (1C), 103.72 (1C), 99.63 (1C), 98.57 (1C), 96.92 (2C), 95.39 (1C), 93.97 (2C), 93.82 (2C), 71.33 (1C), 71.10 (1C).

Example 13: Preparation of 4,14-O,O-Dibenzoyl PFF-A (4)

To phlorofucofuroeckol-A (200 mg, 0.332 mmol) in a round-bottom flask under $N_2$ atmosphere was added 50.81 µL of pyridine (0.631 mmol) and 50 mL of dry acetone. After stirring for 10 minutes benzoyl chloride (73.28 µL, 0.631 mmol) in small portions was added. The reaction mixture was stirred at room temperature for 16 h and diluted with EtOAc; washed with 1% aqueous HCl, water, and saturated aqueous NaCl; dried over $MgSO_4$; and concentrated in vacuo. The crude compound was purified by column chromatography (methanol:chloroform=1:50) to afford 4,14-O, O-dibenzoyl PFF-A (102 mg, 38%) as a pale yellow powder.

TLC $R_f$=0.64 (Chloroform:Methanol:Water=60:30:4); $^1$H-NMR (600 MHz, DMSO-$d_6$) (9.93 (s, 1H), 9.90 (s, 1H), 9.17 (s, 2H), 9.16 (s, 2H), 8.86 (s, 1H), 8.17 (dd, $J_1$=8.35 Hz, $J_2$=1.28 Hz, 2H), 7.82 (dd, $J_1$=8.35 Hz, $J_2$=1.28 Hz, 2H), 7.80 (tt, $J_1$=7.48 Hz, $J_2$=1.30 Hz, 1H), 7.73 (tt, $J_1$=7.48 Hz, $J_2$=1.30 Hz, 1H), 7.66 (t, J=7.90 Hz, 2H), 7.53 (t, J=7.90 Hz, 2H), 7.42 (s, 1H), 6.58 (s, 1H), 6.29 (s, 1H), 5.87 (t, J=2.06 Hz, 1H), 5.82 (t, J=2.08 Hz, 1H), 5.72 (d, J=2.08 Hz, 2H), 5.56 (d, J=2.06 Hz, 2H); $^{13}$C-NMR (600 MHz, DMSO-$d_6$) (164.24 (1C), 164.19 (1C), 160.36 (1C), 159.48 (1C), 159.42 (2C), 159.28 (2C), 151.55 (1C), 151.10 (1C), 150.90 (1C), 149.52 (1C), 147.50 (1C), 137.58 (1C), 136.38 (1C), 135.62 (1C), 135.04 (1C), 134.41 (1C), 134.28 (1C), 130.63 (2C), 130.25 (1C), 130.01 (1C), 129.34 (2C), 129.24 (2C), 128.34 (1C), 128.31 (1C), 119.83 (1C), 110.78 (1C), 105.82 (1C), 103.88 (1C), 102.38 (1C), 100.22 (1C), 97.01 (1C), 96.91 (1C), 93.85 (2C), 93.65 (2C).

Example 14: Measurement of $IC_{50}$ of Eckol Derivatives Against Acetylcholinesterase and Butyrylcholinesterase Enzyme activities were determined at room temperature. Ultraviolet absorbance was measured spectrophotometrically by a modification of a previously described method (Ellmans et al., Biochemical Pharmacology, 88-95, 1961). To each cuvette was added DTNB (900 µL of 5.55 mM DTNB in 50-mM potassium phosphate buffer, pH 7.4) followed by the addition of substrate (25 µL of a buffer of substrate of varying concentration). The enzymatic reaction was initiated at 25° C. by the addition of enzyme (75 µL of acetylcholinesterase or butyrylcholinesterase, appropriately diluted in 50 mM, pH 7.4, potassium phosphate buffer to give 0.005 unit), and absorbance change was monitored at 412 nm for 60 s. The slope of the absorbance change is the initial rate of an enzyme reaction. Effect of inhibition for each sample was calculated as inhibition (%)=100 (ST/CT)× 100 where CT is the initial rate for a control and ST is the initial rate of a sample. The results are shown in Table 1 below.

TABLE 1

| Compound | Acetylcholinesterase ($IC_{50}$) | Butyrylcholinesterase ($IC_{50}$) |
|---|---|---|
| Eckol | 45.1 | 33.2 |
| 9-O-Methyl Eckol | 34.2 | 10.1 |
| 9-O-Benzyl Eckol | 40.1 | 8.6 |
| Dieckol | 23.4 | 2.5 |
| 9"-O-Methyl Dieckol | 33.2 | 1.4 |
| 9"-O-Benzyl Dieckol | 41.9 | 1.5 |
| Phlorofucofuroeckol A | 94.1 | 1 |
| 14-O-Methyl Phlorofucofuroeckol A | 65.6 | 1.5 |
| 14-O-Benzyl Phlorofucofuroeckol A | 23.2 | 2.5 |

Example 15: Measurement of $IC_{50}$ of Eckol Derivatives Against Beta-Secretase 1

The assay was carried out according to the manufacturer's instruction (Beta Amyloid Cleaving Enzyme) FRET assay kit, RED (Lot. # L0724) from PANVERA® (Madison, Wis.) with modifications. A mixture of 10 µL of substrate, 75 µM Rh-EVNLDAEFK-Quencher, in 50 mM ammonium bicarbonate, 10 µL of beta alpha secretase-1 (1 U/mL) dissolved in 10 µL of assay buffer (50 mM sodium acetate, pH 4.5), was incubated for 60 min at 25° C. in the dark. The mixture was excited at 528 nm, and the light emitted at 620 nm was collected. Fluorescence was measured with a Bio-Tek Microplate fluorescence reader FLx 800 (VT, USA). The inhibition ratio is calculated by following the equation, inhibition (%)=[1 {(S S0)/(C C0)}]×100, where C was the fluorescence of control (substrate, assay buffer, and enzyme) after 60 min of incubation, C0 was the fluorescence of control at zero time, S was the fluorescence of tested samples (substrate, sample solution, and enzyme) after 60 min of incubation, and S0 is the fluorescence of tested samples at zero time. The beta alpha secretase-1 inhibitor, Z-Val-Leu-Leu-CHO, is used as a positive control. A buffer containing 10% DMSO was a negative control. The results are shown in Table 2 below.

TABLE 2

| Compound | Beta alpha secretase-1 ($IC_{50}$) |
|---|---|
| Eckol | 12.5 |
| 9-O-Methyl Eckol | 6.7 |
| 9-O-Benzyl Eckol | 9 |
| Dieckol | 2.3 |
| 9"-O-Methyl Dieckol | 1.2 |
| 9"-O-Benzyl Dieckol | 1.7 |
| Phlorofucofuroeckol A | 2.1 |
| 14-O-Methyl Phlorofucofuroeckol A | 1.5 |
| 14-O-Benzyl Phlorofucofuroeckol A | 1.1 |

Example 16: Calculation of Log P and Log S of Eckol Derivatives

Log P is a crucial factor for penetration of the blood brain barrier. Log S measures water solubility which is essential property in systemic drug bioavailability. Log P and Log S can be modified by eckol derivatization to provide optimal compounds for pharmacological applications. Log P and Log S were calculated using ALOGPS 2.1 (http://www.vc-clab.org/lab/alogps/), which is a free program provided by the Virtual Computation Chemistry Laboratory (Tetko et al., *Virtual computational chemistry laboratory—design and description*, J. Comput. Aid. Mol. Des., 2005, 19, 453-63. The results are shown in Table 3 below.

TABLE 3

| Compound | Log P | Log S |
|---|---|---|
| Eckol | 2.71 | −3.44 |
| 9-O-Methyl Eckol | 3.15 | −3.68 |
| 9-O-Benzyl Eckol | 4.44 | −4.44 |
| Dieckol | 4.18 | −4.19 |
| 9"-O-Methyl Dieckol | 5.02 | −4.64 |
| 9"-O-Benzyl Dieckol | 5.74 | −4.64 |
| 9"-O-Trifluoromethyl Dieckol | 5.56 | −4.52 |
| Dieckol 9"-O—CO(CH$_2$)$_5$OH | 5.62 | −4.58 |
| Dieckol 9"-O—COCH$_2$CO$_2$CH$_3$ | 4.93 | −4.35 |
| Dieckol 9"-O—CO(CH$_2$)$_4$SH | 5.62 | −4.58 |
| Phlorofucofuroeckol A | 4.15 | −3.19 |
| 14-O-Methyl Phlorofucofuroeckol A | 4.42 | −3.24 |
| 14-O-Benzyl Phlorofucofuroeckol A | 5.27 | −3.60 |

What is claimed is:

1. A compound of structural Formula (IV):

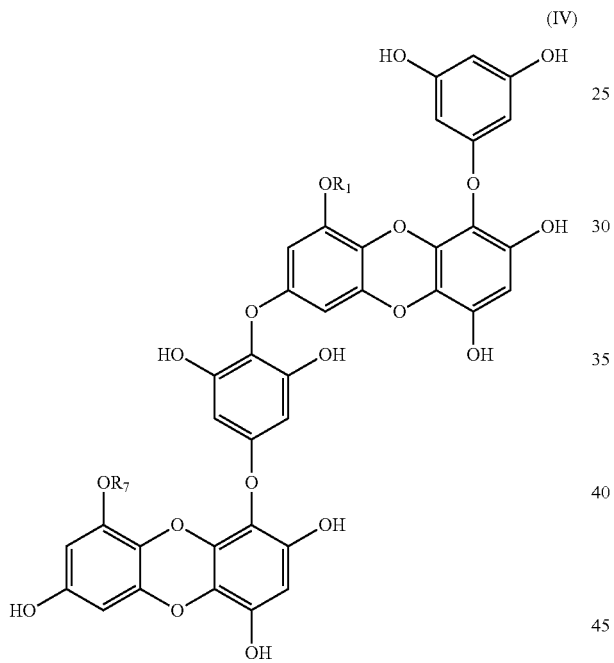

wherein $R_1$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$— or $R_{11}OC(O)$—; $R_7$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{70}C(O)$— or $R_{71}OC(O)$—; and $R_{10}$, $R_{11}$, $R_{70}$ and $R_{71}$ are independently alkyl or aryl.

2. The compound of claim 1, wherein $R_{10}$, $R_{11}$, $R_{70}$ and $R_{71}$ are independently methyl or phenyl.

3. The compound of claim 1, wherein $R_1$ is hydrogen, —CF$_3$, —CH$_2$Ph, —C(O)CH$_3$, —C(O)Ph, —C(O)OCH$_3$, —C(O)OPh, —CH$_2$OCH$_3$ or —CH$_2$C≡CH and $R_7$ is —CH$_3$, —CF$_3$, —CH$_2$Ph, —C(O)CH$_3$, —C(O)Ph, —C(O)OCH$_3$, —C(O)OPh, —CH$_2$OCH$_3$ or —CH$_2$C≡CH.

4. The compound of claim 1, wherein $R_1$ is hydrogen and $R_7$ is —CH$_3$, —CF$_3$, —CH$_2$Ph, —C(O)OCH$_3$, —C(O)CH$_3$, —C(O)Ph, —C(O)OPh, —CH$_2$OCH$_3$ or —CH$_2$C≡CH.

5. The compound of claim 1, wherein $R_1$ is hydrogen and $R_7$ is —CH$_3$, —CF$_3$, —CH$_2$Ph, —C(O)OCH$_3$, —C(O)OPh, —CH$_2$OCH$_3$ or —CH$_2$C≡CH.

6. The compound of claim 1, wherein $R_1$ is hydrogen, —CF$_3$, —CH$_2$Ph, —C(O)OCH$_3$, —C(O)OPh, —CH$_2$OCH$_3$ or —CH$_2$C≡CH and $R_7$ is —CH$_3$, —CF$_3$, —CH$_2$Ph, —C(O)OCH$_3$, —C(O)OPh, —CH$_2$OCH$_3$ or —CH$_2$C≡CH.

7. A method of treating or preventing Alzheimer's disease in a patient comprising administering to the patient in need thereof a therapeutically effective amount of a compound of claim 1.

8. A pharmaceutical composition comprising a compound of claim 1 and a pharmaceutically acceptable vehicle.

9. A compound of structural Formula (VI):

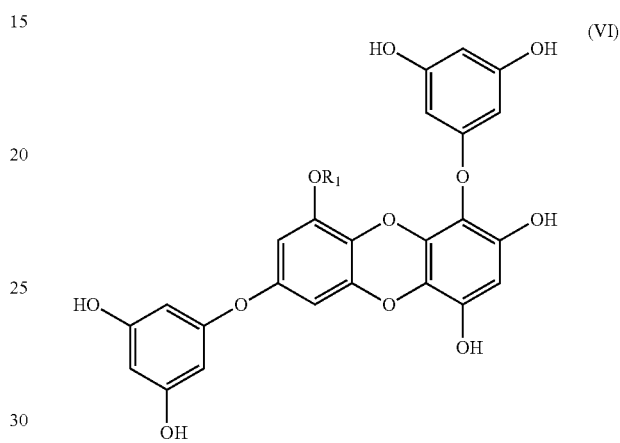

wherein $R_1$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$— or $R_{11}OC(O)$—; and $R_{10}$ and $R_{11}$ are independently alkyl or aryl.

10. The compound of claim 9, wherein $R_{10}$ and $R_{11}$ are independently methyl or phenyl.

11. The compound of claim 9, wherein $R_1$ is —CH$_3$, —CF$_3$, —CH$_2$Ph, —C(O)CH$_3$, —C(O)Ph, —C(O)OCH$_3$, —C(O)OPh, —CH$_2$OCH$_3$ or —CH$_2$C≡CH.

12. The compound of claim 9, wherein $R_1$ is —CH$_3$, —CF$_3$, —CH$_2$Ph, —C(O)OCH$_3$, —C(O)OPh, —CH$_2$OCH$_3$ or —CH$_2$C≡CH.

13. A method of treating or preventing Alzheimer's disease in a patient comprising administering to the patient in need thereof a therapeutically effective amount of a compound of claim 9.

14. A pharmaceutical composition comprising a compound of claim 9 and a pharmaceutically acceptable vehicle.

15. A compound of structural Formula (VII):

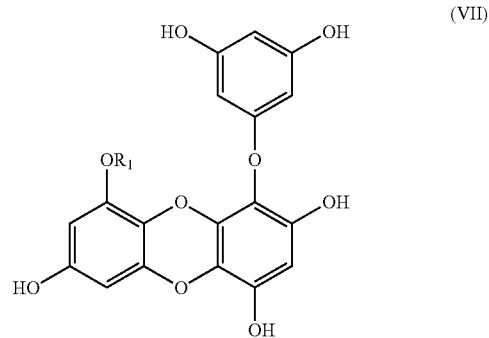

wherein $R_1$ is ($C_2$-$C_{20}$) alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$— or $R_{11}OC(O)$—; and $R_{10}$ and $R_{11}$ are independently alkyl or aryl.

16. The compound of claim 15, wherein $R_{10}$ and $R_{11}$ are independently methyl or phenyl.

17. The compound of claim 15, wherein $R_1$ is —$CH_3$, —$CF_3$, —$CH_2Ph$, —$C(O)CH_3$, —$C(O)Ph$, —$C(O)OCH_3$, —$C(O)OPh$, —$CH_2OCH_3$ or —$CH_2C\equiv CH$.

18. The compound of claim 15, wherein $R_1$ is —$CH_3$, —$CF_3$, —$CH_2Ph$, —$C(O)OCH_3$, —$C(O)OPh$, —$CH_2OCH_3$ or —$CH_2C\equiv CH$.

19. A method of treating or preventing Alzheimer's disease in a patient comprising administering to the patient in need thereof a therapeutically effective amount of a compound of claim 15.

20. A pharmaceutical composition comprising a compound of claim 15 and a pharmaceutically acceptable vehicle.

21. A compound of structural Formula (XI):

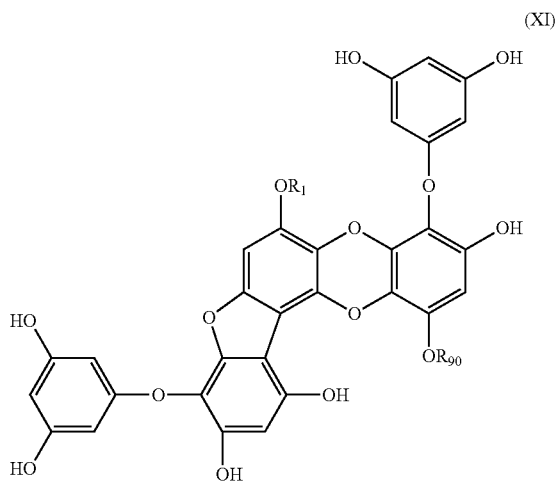

(XI)

wherein $R_1$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$— or $R_{11}OC(O)$—, $R_{90}$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{100}C(O)$, $R_{101}OC(O)$; and $R_{10}$, $R_{11}$, $R_{100}$ and $R_{101}$ are independently alkyl or aryl.

22. The compound of claim 21, wherein $R_{10}$, $R_{11}$, $R_{100}$ and $R_{101}$ are independently methyl or phenyl.

23. The compound of claim 21, wherein $R_1$ is —$CH_2C(O)(CH_2)_5OH$, —$CH_2C(O)(CH_2)_5SH$, —$CH_2C(O)CH_2CO_2CH_3$ and $R_{90}$ is hydrogen.

24. The compound of claim 21, wherein $R_1$ is —$CH_3$, —$CF_3$, —$CH_2Ph$, —$C(O)CH_3$, —$C(O)Ph$, —$C(O)OCH_3$, —$C(O)OPh$, —$CH_2OCH_3$ or —$CH_2C\equiv CH$ and $R_{90}$ is hydrogen, —$CH_3$, —$CF_3$, —$CH_2Ph$, —$C(O)CH_3$, —$C(O)Ph$, —$C(O)OCH_3$, —$C(O)OPh$, —$CH_2OCH_3$ or —$CH_2C\equiv CH$.

25. The compound of claim 21, wherein $R_1$ is —$CH_3$, —$CF_3$, —$CH_2Ph$, —$C(O)OCH_3$, —$C(O)OPh$, —$CH_2OCH_3$ or —$CH_2C\equiv CH$ and $R_{90}$ is hydrogen, —$CH_3$, —$CF_3$, —$CH_2Ph$, —$C(O)OCH_3$, —$C(O)OPh$, —$CH_2OCH_3$ or —$CH_2C\equiv CH$.

26. A method of treating or preventing Alzheimer's disease in a patient comprising administering to the patient in need thereof a therapeutically effective amount of a compound of claim 21.

27. A pharmaceutical composition comprising a compound of claim 21 and a pharmaceutically acceptable vehicle.

28. A compound of structural Formula (XI):

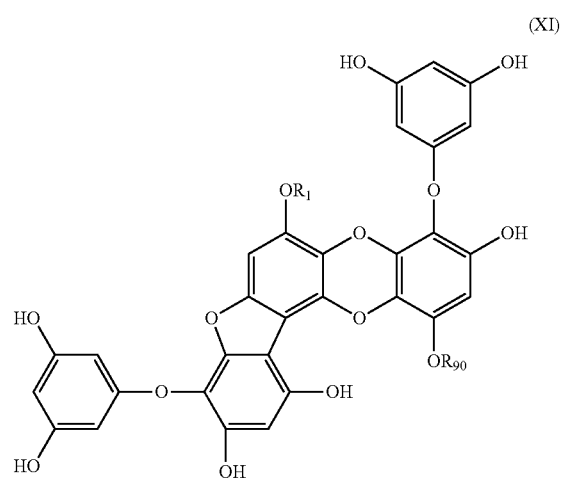

(XI)

wherein $R_1$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$— or $R_{11}OC(O)$—, $R_{90}$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{100}C(O)$, $R_{101}OC(O)$; and $R_{10}$, $R_{11}$, $R_{100}$ and $R_{101}$ are independently alkyl or aryl.

29. The compound of claim 28, wherein $R_{10}$ and $R_{11}$ are independently methyl or phenyl.

30. The compound of claim 28, wherein $R_1$ is hydrogen, —$CH_3$, —$CF_3$, —$CH_2Ph$, —$C(O)CH_3$, —$C(O)Ph$, —$C(O)OCH_3$, —$C(O)OPh$, —$CH_2OCH_3$ or —$CH_2C\equiv CH$ and $R_9$ is —$CH_3$, —$CF_3$, —$CH_2Ph$, —$C(O)CH_3$, —$C(O)Ph$, —$C(O)OCH_3$, —$C(O)OPh$, —$CH_2OCH_3$ or —$CH_2C\equiv CH$.

31. The compound of claim 28, wherein $R_1$ is hydrogen, —$CH_3$, —$CF_3$, —$CH_2Ph$, —$C(O)OCH_3$, —$C(O)OPh$, —$CH_2OCH_3$ or —$CH_2C\equiv CH$ and $R_9$ is —$CH_3$, —$CF_3$, —$CH_2Ph$, —$C(O)OCH_3$, —$C(O)OPh$, —$CH_2OCH_3$ or —$CH_2C\equiv CH$.

32. A method of treating or preventing Alzheimer's disease in a patient comprising administering to the patient in need thereof a therapeutically effective amount of a compound of claim 28.

33. A pharmaceutical composition comprising a compound of claim 28 and a pharmaceutically acceptable vehicle.

34. A compound of structural Formula (VIII):

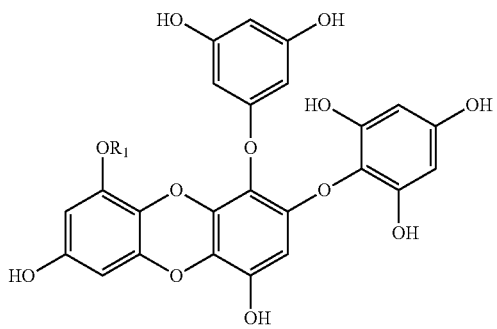

(VIII)

wherein $R_1$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, $R_{10}C(O)$— or $R_{11}OC(O)$—; and $R_{10}$ and $R_{11}$ are independently alkyl or aryl.

35. The compound of claim 34, wherein $R_{10}$ and $R_{11}$ are independently methyl or phenyl.

36. The compound of claim 34, wherein $R_1$ is —$CH_3$, —$CF_3$, —$CH_2Ph$, —$C(O)CH_3$, —$C(O)Ph$, —$C(O)OCH_3$, —$C(O)OPh$, —$CH_2OCH_3$ or —$CH_2C\equiv CH$.

37. The compound of claim 34, wherein $R_1$ is —$CH_3$, —$CF_3$, —$CH_2Ph$, —$C(O)OCH_3$, —$C(O)OPh$, —$CH_2OCH_3$ or —$CH_2C\equiv CH$.

38. A method of treating or preventing Alzheimer's disease in a patient comprising administering to the patient in need thereof a therapeutically effective amount of a compound of claim 34.

39. A pharmaceutical composition comprising a compound of claim 34 and a pharmaceutically acceptable vehicle.

* * * * *